(12) United States Patent
Borg et al.

(10) Patent No.: US 9,517,118 B1
(45) Date of Patent: Dec. 13, 2016

(54) ORTHODONTIC FLOSSER

(71) Applicants: N. Michelle Borg, Paradise, CA (US); John O. H. Niswonger, Calabasas, CA (US)

(72) Inventors: N. Michelle Borg, Paradise, CA (US); John O. H. Niswonger, Calabasas, CA (US)

( * ) Notice: Subject to any disclaimer, the term of this patent is extended or adjusted under 35 U.S.C. 154(b) by 621 days.

(21) Appl. No.: 14/078,509

(22) Filed: Nov. 12, 2013

Related U.S. Application Data

(63) Continuation-in-part of application No. 13/196,302, filed on Aug. 2, 2011, now Pat. No. 8,671,958, which is a continuation-in-part of application No. 12/904,058, filed on Oct. 13, 2010, now Pat. No. 8,387,629.

(60) Provisional application No. 61/251,609, filed on Oct. 14, 2009.

(51) Int. Cl.
*A61C 15/00* (2006.01)
*A61C 15/04* (2006.01)
*B65H 69/04* (2006.01)

(52) U.S. Cl.
CPC .......... *A61C 15/046* (2013.01); *B65H 69/04* (2013.01)

(58) Field of Classification Search
CPC ................................................ A61C 15/046
USPC .................................................. 132/323–327
See application file for complete search history.

(56) References Cited

U.S. PATENT DOCUMENTS

| | | | | |
|---|---|---|---|---|
| 3,734,107 | A * | 5/1973 | Thierman | A61C 15/046 132/325 |
| 5,860,434 | A * | 1/1999 | Sines | A61C 15/046 132/323 |
| 5,947,133 | A * | 9/1999 | Kossak | A61C 15/046 132/323 |
| 2004/0255972 | A1 * | 12/2004 | Chen | A61C 15/046 132/325 |
| 2007/0204879 | A1 * | 9/2007 | Chen | A61C 15/046 132/325 |

* cited by examiner

*Primary Examiner* — Todd E Manahan
*Assistant Examiner* — Brianne Kalach
(74) *Attorney, Agent, or Firm* — Ronald L. Rohde

(57) ABSTRACT

An orthodontic flosser comprising an elongated handle and a head coupled to the handle is disclosed. A projection extend for suspending floss is sized for insertion of floss between a wire affixed to a tooth and the tooth. A source spool of fresh floss is configured to feed fresh floss incrementally into suspension from the projection while a take-up bobbin is configured for taking up used floss and applying tension to the suspended floss. A button may be used for releasing the source spool to rotate, and for holding the source spool against rotation. The source spool and take-up bobbin may be disposed in separated chambers to reduce cross contamination. A retie flange in the take-up bobbin and a retie slot in a take-up chamber are configured for retying broken floss around a spindle of the take-up bobbin.

18 Claims, 16 Drawing Sheets

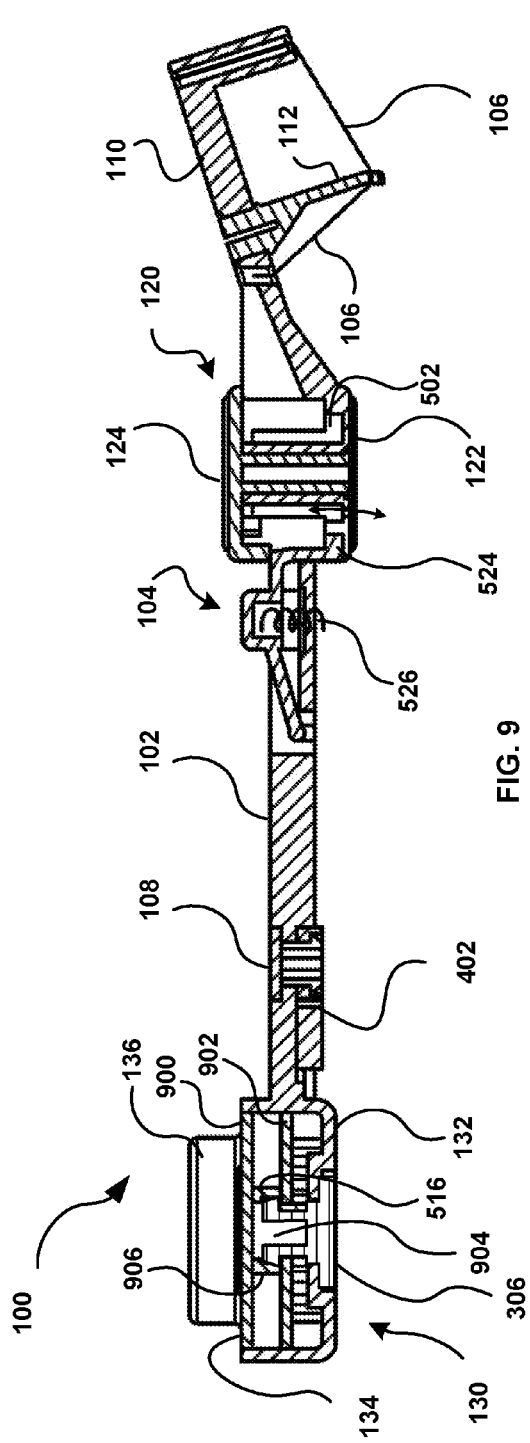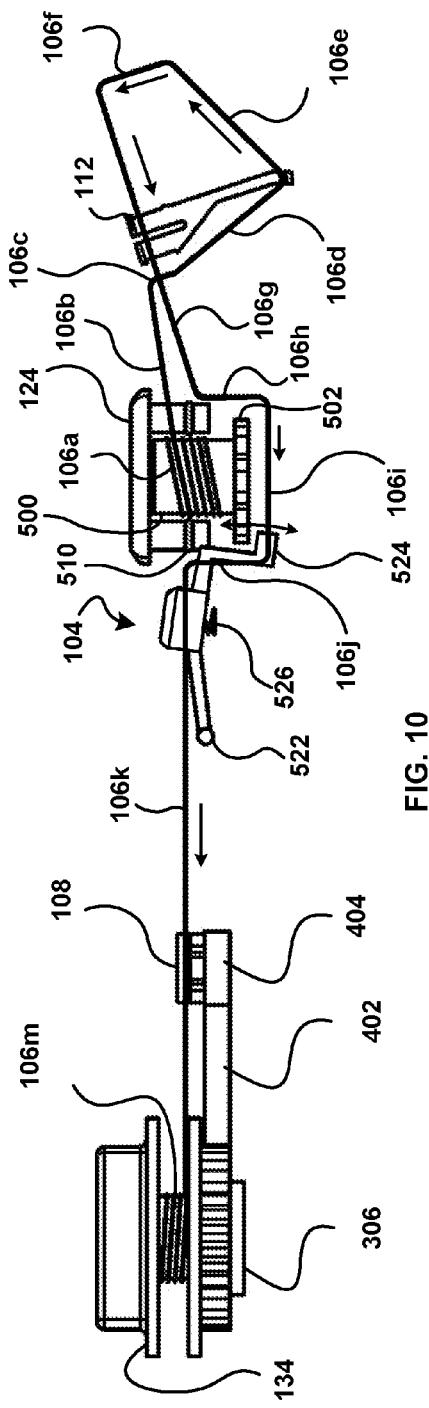

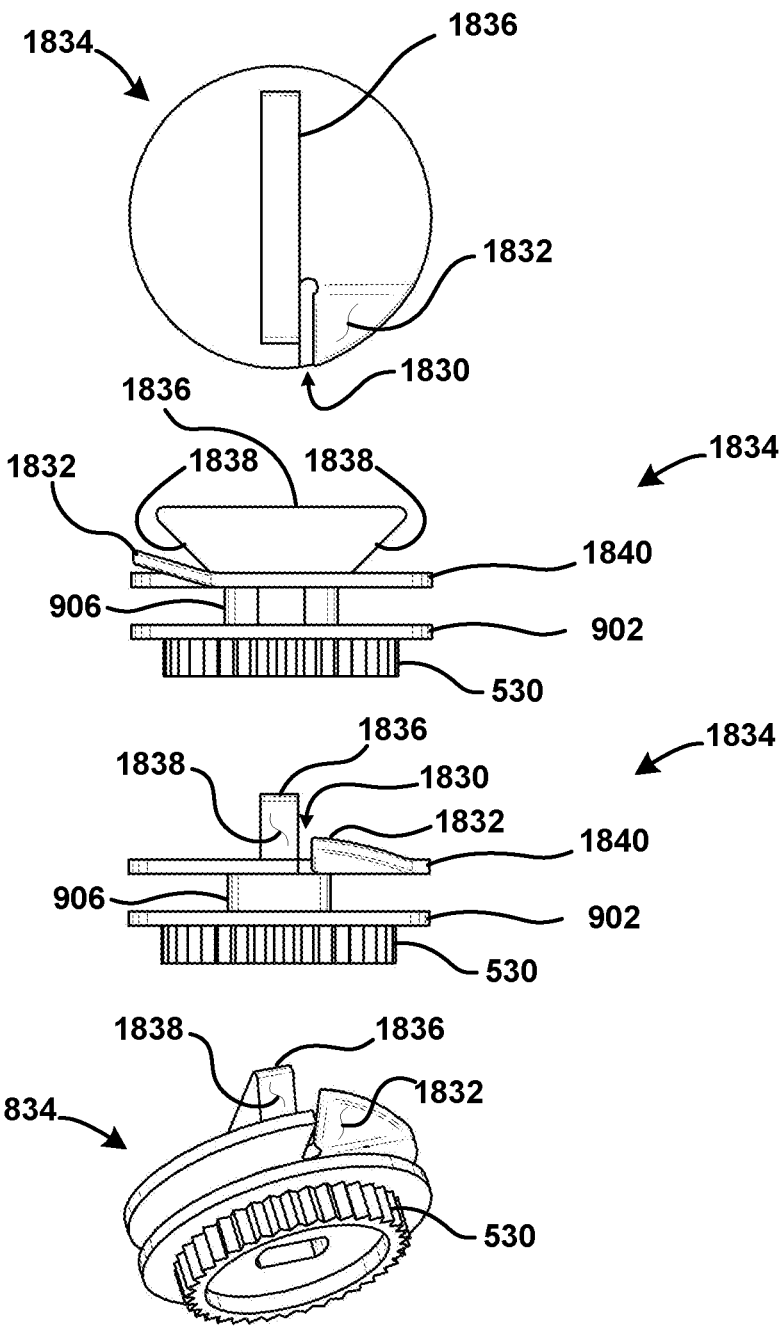

FIG. 23A
FIG. 24A
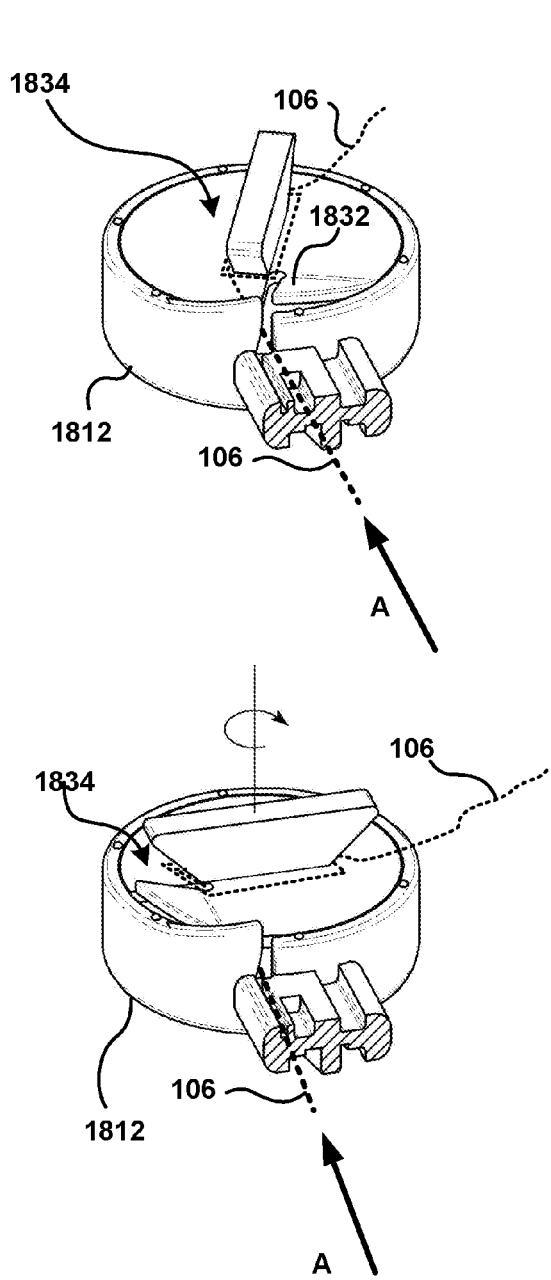
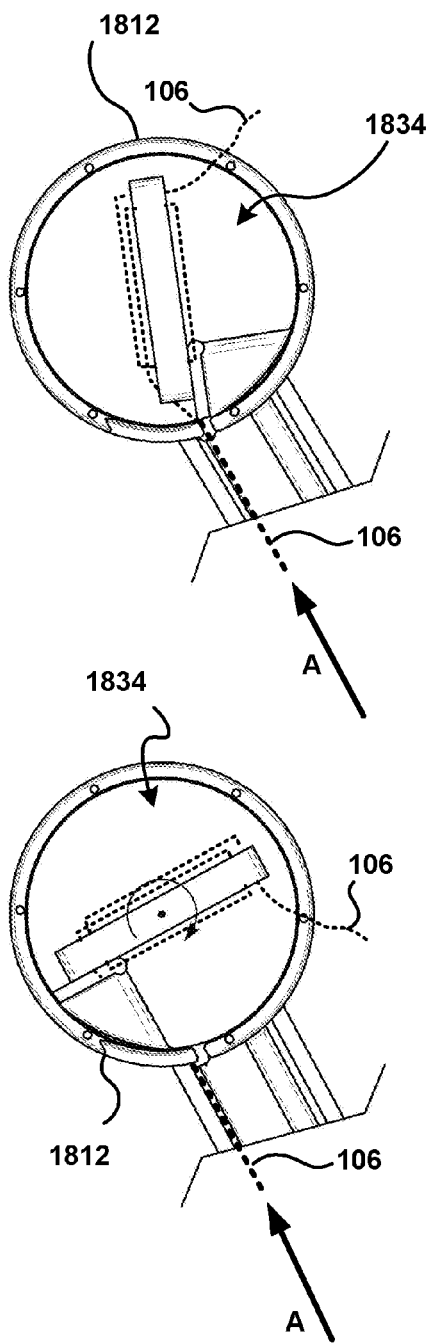
FIG. 23B
FIG. 24B

ORTHODONTIC FLOSSER

CROSS-REFERENCE TO RELATED APPLICATIONS

The present application is a continuation in part of pending U.S. patent application Ser. No. 13/196,302, filed on Aug. 2, 2011 titled "ORTHODONTIC FLOSSER," which in turn is a continuation in part of U.S. patent application Ser. No. 12/904,058, filed on Oct. 13, 2010 titled "ORTHODONTIC FLOSSER" (now U.S. Pat. No. 8,387,629, issued Mar. 5, 2013), which in turn claims priority and benefit to U.S. provisional patent application Ser. No. 61/251,609 filed on Oct. 14, 2009 titled "ORTHODONTIC FLOSSER," and is related to U.S. provisional patent application Ser. No. 61/241,281, filed on Sep. 10, 2009 and titled "ANTI-MICROBIAL ORTHODONTIC FLOSS." All of the above applications are incorporated by reference herein in their entirety.

BACKGROUND

Field of the Application

The present application relates generally to a flossing apparatus, and more particularly to an orthodontic flosser.

Description of Related Art

Flossing is particularly important for people who have braces. Braces typically include brackets bonded to the surfaces of two or more teeth and a wire or archwire affixed to the brackets. Flossing around braces may be accomplished by threading the floss between the braces and the teeth and then maneuvering a length of the floss into contacts between adjacent teeth. Upon flossing around a pair of teeth and braces, the floss is generally pulled out and then threaded into another position for the next pair of teeth. Unfortunately, threading, inserting, manipulating the floss around the braces, and removing the floss for each pair of teeth can be difficult and time consuming. Maintaining tension on the floss while manipulating the floss between teeth and around braces involves a degree of dexterity and skill that is often beyond the ability of many children and even adults. Frustration due to the difficulty of acquiring skills, manipulating the floss, and the extra time involved in threading and removing the floss can discourage flossing. The purpose of flossing is to remove debris and contamination from contacts between teeth and surfaces around braces to prevent interproximal tooth decay and gum disease. Debris includes particulate matter, dental plaque, and bio films. Contamination includes bacteria and nutrients for the bacteria. Dental plaque tends to adhere to surfaces such as teeth and wires. Floss generally picks up debris and contamination from surfaces of the teeth and the braces in the removal process. Unfortunately, the floss can then redistribute the debris and bacteria to other teeth, interproximal spaces, and braces around the mouth, thus, causing further spreading of tooth decay and gum disease.

SUMMARY

A flosser is described. The flosser includes a handle and a head including a first and second floss support for suspending floss there between, the second floss support including an aperture sized for feeding the floss into suspension between the first and second floss support, the second floss support shaped for insertion of the aperture into a space between the wire brace and the two teeth for cleaning the contact between the two teeth using suspended floss. A source chamber may be coupled to a first end of the handle and configured to support the head, the source chamber may enclose a source spool for dispensing floss to the aperture in the second floss support. A button may be configured to release tension on the floss. A take-up chamber may be coupled to a second end of the handle opposite the source chamber, the take-up chamber and the source chamber being external to the handle, the take-up chamber having a retie slot proximate the handle, the retie slot including a capture fence extending above a rim of the take-up chamber and a guide edge configured to bias floss into the retie slot. A take-up bobbin for receiving used floss may be disposed in the take-up chamber, the take-up bobbin including a retie flange extending at an angle above the rim of the take-up chamber, the retie flange and the guide edge configured to trap the floss and to urge the floss into the retie slot while rotating the take-up bobbin. The take-up bobbin may include a grip disposed on the take-up bobbin, the grip configured for wrapping a broken end of the floss around the grip.

Various embodiments of the technology include a method for retying broken floss on a flosser including a pair of projections for suspending floss. The method includes rotating a take-up bobbin including a retie channel disposed in an upper flange to align the retie channel with a retie slot disposed in a take-up chamber, the retie channel adjacent a retie flange extending upward from and above the upper flange and wrapping an end of the broken floss around a grip of a take-up bobbin. The method further includes pressing a button to release source spool to rotate freely while rotating the take-up bobbin to position a portion of the retie flange above the floss after wrapping the end of the broken floss around the grip and then further rotating the take-up bobbin to urge the floss against a guide edge of the retie slot, and then still further rotating the take-up bobbin to close the top of the retie slot using the upper flange to trap floss in a space between the upper flange and a lower flange. After closing the top of the retie slot, the method further includes rotating the take-up bobbin at least two complete turns to draw floss into the space between the upper flange and the lower flange, and to wrap the floss around a spindle of the take-up bobbin until the floss is secured to the spindle while still pressing the button. The method then includes releasing the button, and rotating the take-up bobbin to apply tension to the floss suspended between the pair of projections.

Various embodiments of the technology include an apparatus for cleaning teeth, the apparatus having an elongated handle configured for dispensing fresh floss, a head coupled to the handle at an upward angle and a pair of projections depending in the plane of the upward angle downward from the head and configured to slidably suspend fresh floss under tension. The apparatus further includes a first spool supported on the elongated handle and configured to provide fresh floss to the pair of projections and to maintain resistance to tension on the fresh floss during use of the fresh floss for cleaning teeth and a second spool supported on the elongated handle and configured to apply tension to the fresh floss when resistance to tension is maintained at the first spool and to receive used floss from the pair of projections when resistance to tension is released at the first spool. The second spool and take-up chamber including a slot and flange configured for retying broken floss without removing the second spool from the take-up chamber. The apparatus also has a button assembly configured to release resistance to tension at the first spool.

Various embodiments of the technology include a retieble flosser. The flosser includes a head, a source chamber supporting the head, a handle coupled to the source chamber, a take-up chamber coupled to the handle, and a bobbin rotatably disposed in the take-up chamber, the bobbin including an upper flange, a lower flange, a spindle for winding floss between the upper and lower flanges, and a grip for rotating the bobbin. A retie slot may be disposed in the take-up chamber, the retie slot including a capture fence extending above a rim of the take-up chamber, the capture fence configured to constrain floss above the retie slot while wrapping floss around the grip, and a guide edge disposed along one side of the retie slot, the guide edge forming an acute angle configured for forcing floss into the take-up chamber while rotating the bobbin. A retie channel and a retie flange may be disposed in the upper flange; the retie flange forming one edge of the retie channel, the retie flange extending above a plane of the upper flange and above a rim of the take-up chamber, the retie flange configured for forcing floss against the guide edge and into the retie slot while rotating the bobbin using the grip, the grip further configured for receiving at least two wraps of floss around the grip and holding wraps of floss adjacent the upper flange while rotating the bobbin.

BRIEF DESCRIPTION OF THE DRAWINGS

FIG. 9 is a side cross section of the flosser of FIG. 1 along line b-b of FIG. 3.

FIG. 10 is a side elevation of internal parts of the flosser of FIG. 1.

FIG. 22A is a top plan view of the bobbin of FIG. 18.

FIG. 22B is a side elevation view of the bobbin of FIG. 18.

FIG. 22C is a front elevation view of the bobbin of FIG. 18.

FIG. 22D is a bottom perspective view of the bobbin of FIG. 18.

FIGS. 23A-23D are front perspective views illustrating application of a rotation to the bobbin for retying floss on the flosser of FIG. 18.

FIGS. 24A-24D are top plan views of the corresponding positions of the bobbin of FIGS. 23A-23D, respectively, for illustrating the application of the rotation to the bobbin for retying floss on the flosser of FIG. 18.

DETAILED DESCRIPTION

Figure 1:
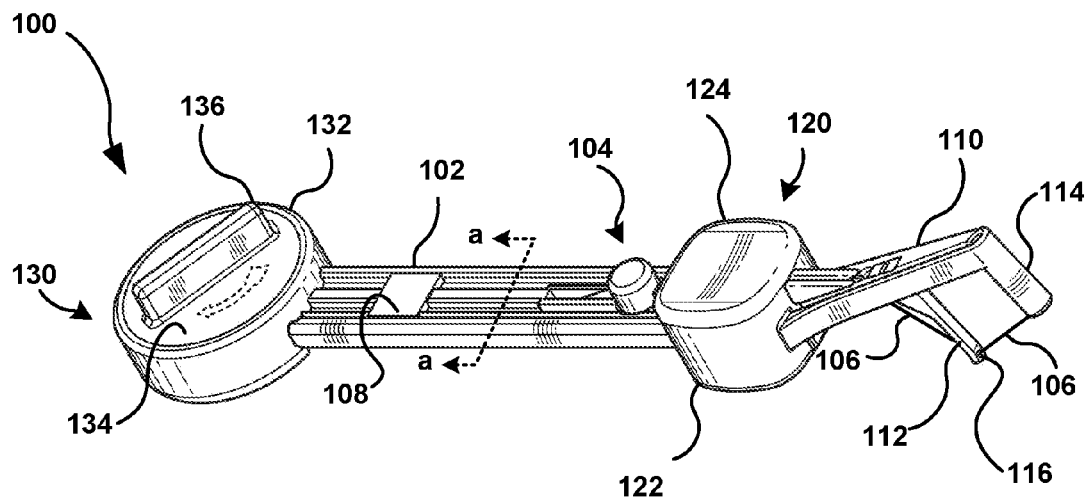
FIG. 1 is a top perspective view of an embodiment of a flosser, in accordance with aspects of the technology.
Figure 2:
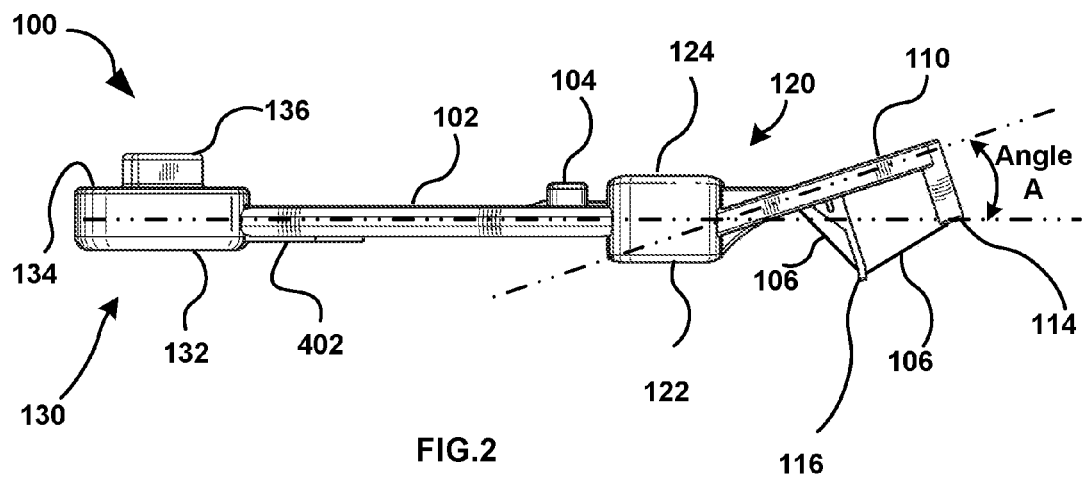
FIG. 2 is a right side elevation of the flosser of FIG. 1.

FIG. 1 is a top perspective view of an embodiment of a flosser 100, in accordance with aspects of the technology. FIG. 2 is a side elevation of the flosser 100 of FIG. 1. The flosser 100 includes a handle 102, a head 110, a source assembly 120 for dispensing floss 106 to the head 110 before use (fresh floss), and a receiving assembly or take-up assembly 130 for collecting floss 106 from the head 110 after it has been used (used floss). The handle 102 is configured to support the source assembly 120, the take-up assembly 130, and the head 110. The head 110 of FIG. 1 extends from the source assembly 120 and includes a support or projection 112 and a support, feed guide, or guide 114. Floss 106 may be supported and suspended between projection 112 and the guide 114 (suspended floss). In various embodiments, the head 110 is coupled to the handle, the take-up assembly 130 and/or the source assembly 120. The guide 114 of FIG. 1 is in the shape of a tube. However, other shapes include a trough, a channel, aperture on a projection, etc. The source assembly 120 is illustrated as being disposed at an end of the handle 102 adjacent the head 110. However, the source assembly 120 may be disposed at various locations along the handle 102. Similarly, the take-up assembly 130 may be disposed at various locations along the handle 102. In some embodiments, the positions of the source assembly 120 and the take-up assembly 130 may be reversed with respect to those illustrated in FIG. 1.

The head 110 may be disposed at upward angle A from the handle 102, as illustrated in FIG. 2. A dotted line represents an axis of the handle 102 and another dotted represents an axis of the head 110 in FIG. 2. The dotted lines are for assisting in visualization of the angle A and are not part of the flosser 100. The upward angle A between the handle 102 and the head 110 may promote ergonomics and use of the flosser 100. For example, the angle may improve visibility of the floss 106 under the handle 102 during use. In various embodiments, the angle A is about 10, 11, 12, 13, 14, 15, 16, 17, 18, 19, 20, 23, 25 or more degrees. The projection 112 and the guide 114 may depend downward from the head in about the plane of the angle A between the head 110 and the handle 102. The projection 112 and the guide 114 may be about normal to the head 110 and about parallel to each other. The projection 112 of FIG. 2 is longer than the feed guide 114. This may also promote ergonomics and use of the flosser 100. For example, a shorter feed guide 114 may reduce interference with a tongue and/or the roof of the mouth of a user and increase range of motion of the projection 112. In various embodiments, the projection 112 is 2, 3, 4, 5, 6, 7, 8, 9, 10 or more millimeters longer than the feed guide 114.

A support aperture or projection aperture 116 may be disposed near a tip of the projection 112 and configured to support floss 106. Floss 106 may be suspended between the tube of the feed guide 114 and the support aperture 116. The support aperture 116 is configured to support the floss 106 near the tip of the projection 112. The support aperture 116 may be sized for floss 106 to slide through freely or with a desired resistance. The flosser 100 further includes a button assembly 104 disposed on the handle 102. The button assembly 104 engage and disengaged a spool in the source assembly 120 as described more fully elsewhere herein.

The source assembly 120 is configured to enclose and floss 106 from contamination and debris before use. The source assembly 120 is further configured to pay out floss 106 to the projection 112 while the button assembly 104 is disengaged. The source assembly 120 includes a source chamber 122, a lid 124, and a spool (illustrated elsewhere herein). The source chamber 122 and the lid 124 may enclose the floss 106 and prevent contamination and debris from splashing and falling on enclosed floss 106. The take-up assembly 130 is configured to receive and accumulate the floss 106 after use. The take-up assembly 130 includes a take-up chamber 132, and take-up (or receiving) bobbin (or spool) 134. The bobbin 134 includes a bobbin grip 136 configured for use in rotating the bobbin 134 to wind the floss 106 around the bobbin 134 after use and draw the floss 106 through the flosser 100 while the button assembly 104 is actuated. Winding the floss 106 around a spindle of the bobbin 134 using the grip 136 may further serve to apply tension to the floss 106 while the button assembly 104 is engaged. The bobbin 134 and take-up chamber 132 are configured to enclose floss 106 to contain contamination and debris disposed on the floss 106 during use. The source chamber 122 and take-up chamber 132 may be physically separated structures disposed along the handle 102 to reduce cross contamination of debris and bacteria from the take-up chamber 132 to the source chamber 122. The source chamber 122 and take-up chamber 132 may disposed at opposite ends of the handle 102 or separated by a portion of the handle 102.

Figure 3:
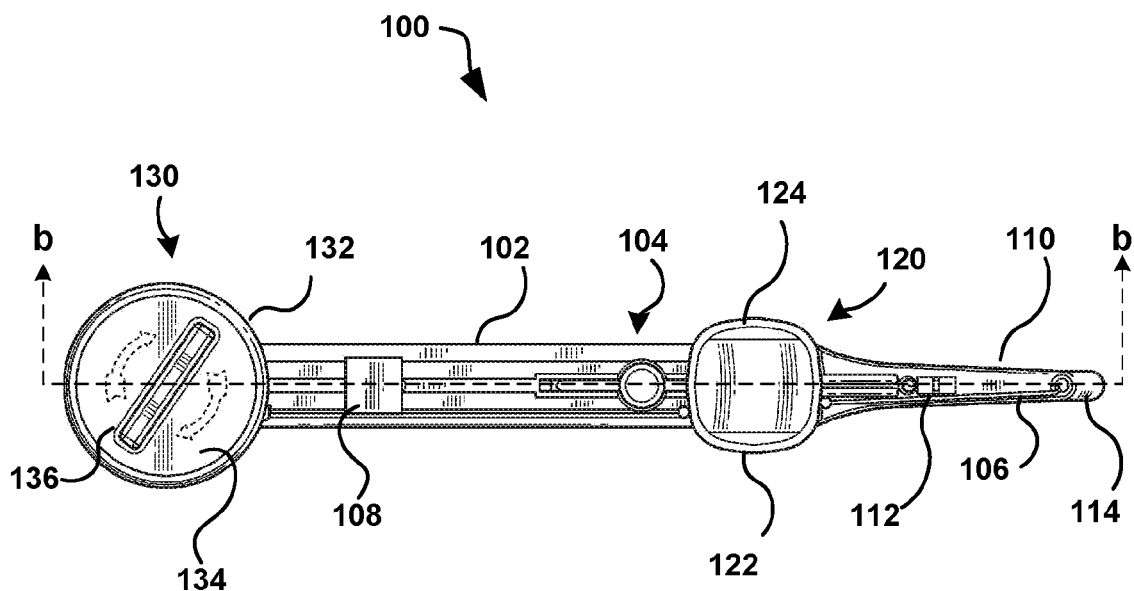
FIG. 3 is a top plan view of the flosser of FIG. 1.
Figure 4:
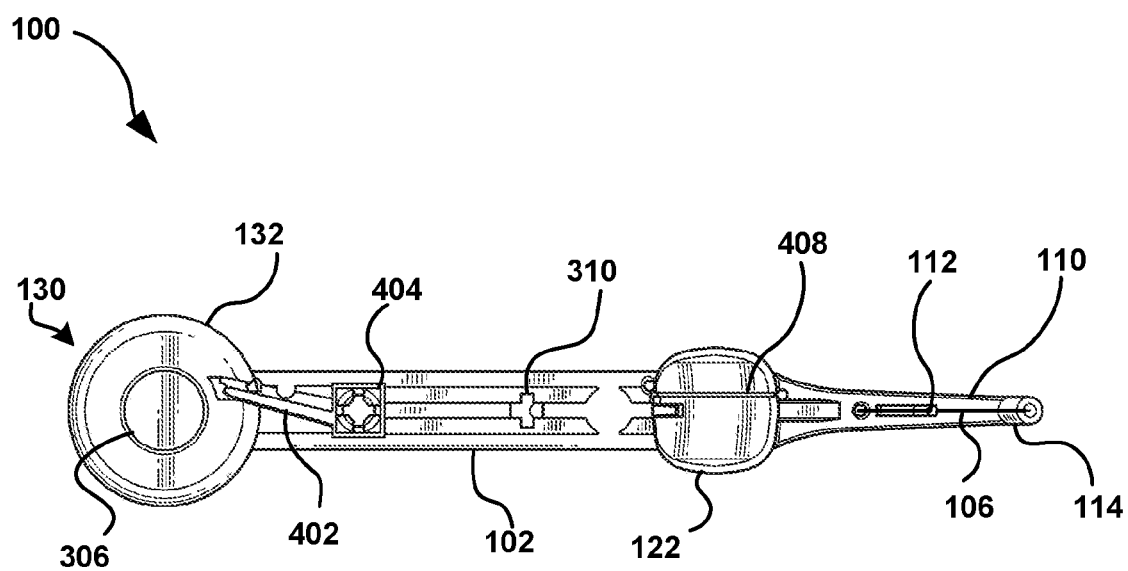
FIG. 4 is a bottom plan view of the flosser of FIG. 1.

FIG. 3 is a top plan view of the flosser 100 of FIG. 1. FIG. 4 is a bottom plan view of the flosser 100 of FIG. 1. FIG. 4 illustrates a pawl 402 and a pawl mount 404. The pawl 402 is configured to engage a sprocket disposed on the bobbin 134 to provide for one-way rotation of the bobbin 134. The pawl mount 404 illustrated in FIG. 4 (also FIGS. 1 and 3) may secure the pawl 402 to the handle 102. A bobbin lock 306 may secure the bobbin 134 within the take-up chamber 132. A button socket 310 may secure the button assembly 104 rotatably to the handle 102. A groove 408 may provide a path for slidable movement of floss 106 between the head 110 and the handle 102 after use.

Figure 5:
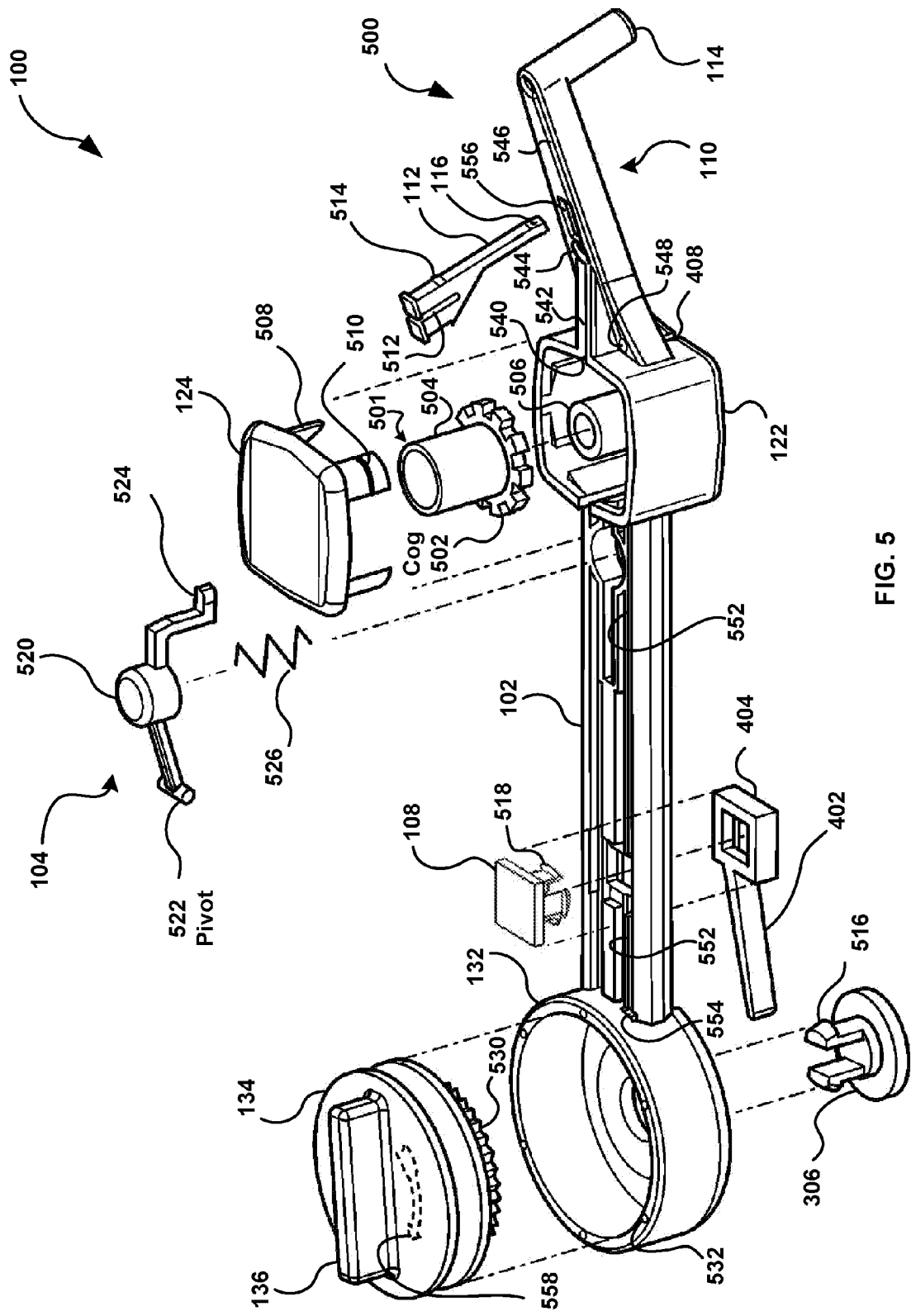
FIG. 5 is an exploded perspective view illustrating exemplary internal components the flosser of FIG. 1, in accordance with aspects of the technology.
Figure 6:
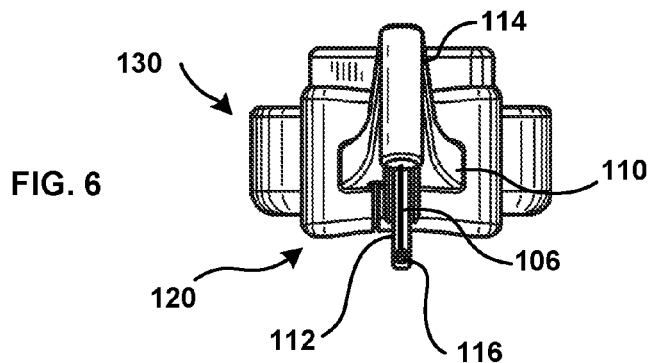
FIG. 6 is an enlarged front elevation of the flosser of FIG. 1.
Figure 7:
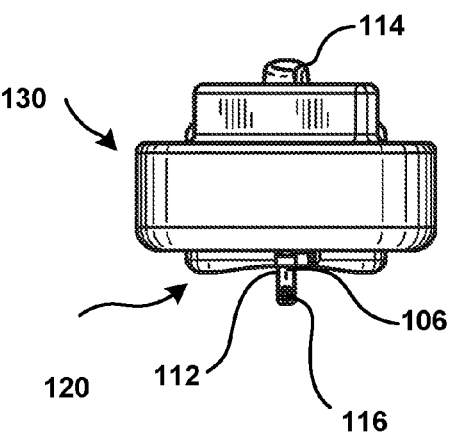
FIG. 7 is an enlarged rear elevation of the flosser of FIG. 1.

FIG. 5 is an exploded perspective view illustrating exemplary internal components the flosser 100 of FIG. 1, in accordance with aspects of the technology. FIG. 6 is an enlarged front elevation of the flosser 100 of FIG. 1. FIG. 7 is an enlarged rear elevation of the flosser 100 of FIG. 1. A body 500 comprises the handle 102, the source chamber 122, take-up chamber 132, and the head 110. The body 500 of FIG. 5 is illustrated as having been fabricated from a single piece of material, for example using injection molding processes. However, the body may be fabricated using multiple connected pieces.

The source assembly 120 of FIG. 5 further includes a source spool 501. The source spool 501 includes a spindle 504 upon which floss 106 may be wound for dispensing and use. In some embodiments, the floss is wound before assembly of the source spool 501 into the source chamber 122. In various embodiments, 1, 2, 3, 4, 5, 6, 7, 8, 10, 15, 20, or more meters of floss may be wound on the source spool 501. A cog 502 is configured to control unwinding of floss from the spindle 504 for the source spool. The cog 502 is further configured to rotate on a bearing 506. The lid 124 includes locator projections 508 configured to position the lid 124 and engage corners of the source chamber 122. An optional detent 510 disposed on the locator projections 508 may engage a groove within the corners (not illustrated) to secure the lid to the source chamber 122.

A slot or first aperture 540 in the source chamber 122 is configured to feed floss 106 dispensed from the source spool 501 into a channel 542. The channel 542 is configured to provide a path for floss 106 from the first aperture 540 to a second aperture 544. The second aperture 544 is configured to provide a path for floss 106 between the upper surface of the head 110 and the projection aperture 116. The projection 112 of FIG. 1 is a separate component and is configured for insertion into an aperture 556 in the head 110. An optional slot 512 may provide additional flexibility during insertion. An optional detent 514 may secure the projection 112 within the aperture 556. In various embodiments, the projections 112 is secured in the aperture 556 using an interference fit, adhesive, a fastener, a sonic weld, a heat weld, and/or the like. In some embodiments, the head 110 and the projection 112 are fabricated as a single piece.

Figure 8:
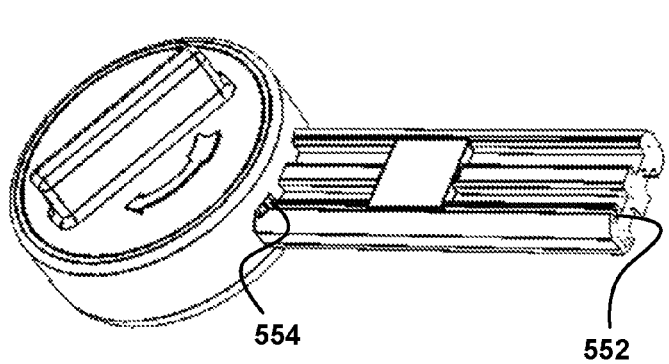
FIG. 8 is a perspective cross section of the handle of the flosser of FIG. 1 taken along line a-a.

A channel 546 may provide a path for floss 106 from the feed guide 114 to a third aperture 548. The third aperture 548 is configured to provide a path for floss 106 from the upper surface of the head 110 to the groove 408. The groove 408 is configured to provide a path for floss 106 from the third aperture 548 to the fourth aperture 550 (illustrated in FIG. 12). The fourth aperture 550 is configured to provide a path for floss 106 from the groove 408 to a handle channel 552. The handle channel 552 may be disposed as a longitudinal channel extending the length or a portion of the length of the handle 102. FIG. 8 is a perspective cross section of the handle of the flosser of FIG. 1 taken along line a-a, illustrating the handle channel 552. The handle channel 552 of FIG. 5 is configured to extend longitudinally along the handle 102 from the fourth aperture 550 to a fifth aperture 554, and provide a path for sliding floss 106. The handle channel 552 may permit the handle 102 to be gripped without touching or interfering with floss 106, thus, permitting free movement or sliding of the floss 106 along the handle 102 through the channel 552. The fifth aperture 554 provides a path through a side of the take-up chamber, from the handle channel 552 to the bobbin 134. Rotation of the bobbin 134 may draw floss 106 from the source spool 501 in a sliding motion through the various apertures (540, 544, 116, 548, 550, and 554), the various channels (542, 546, 552), the groove 408, and the feed guide 114 while the source spool pays out additional floss 106. Edges of the various apertures, channels, grooves, and guides may include a radius for reducing friction between floss 106 and the flosser 100.

The button assembly 104 of FIG. 5 includes a button 520, a pivot 522, an engagement pawl 524, and a spring 526. The pivot is configured to rotate within the button socket 310. The spring 526 may bias the button assembly 104 in the engagement position when the button 520 is not pressed. The engagement pawl 524 is configured to engage the cog 502 and prevent rotation of the source spool 501 when the button 520 is released and the button assembly 104 is in the engagement position. The engagement pawl 524 may hold the source spool 501 against tension on the floss 106. The button 520 may be pressed to move the button assembly to the disengagement position, thus, releasing the source spool 501 to rotate freely. Tension on the floss 106 may cause the source spool 501 to rotate and dispense floss 106. Rotation of the take-up bobbin 134 may cause the source spool 501 to rotate and dispense additional floss 106. Rotation of the take-up bobbin 134 may cause additional tension to be applied to the floss 106 when the engagement pawl 524 is in the engagement position. An illustration of the button assembly 104 in the engaged position is shown in FIG. 9, as discussed elsewhere herein. An illustration of the button assembly 104 in the disengaged position is shown in FIG. 10, as discussed elsewhere herein.

FIG. 9 is a side cross section of the flosser of FIG. 1 along line b-b of FIG. 3. The bobbin 134 includes an upper flange 900 supporting the grip 136, a lower flange 902 supporting a ratchet 530 and a spindle 906. An optional spindle aperture 904 is disposed in the spindle 906. In some embodiments, the bobbin 134, the upper flange 900, the lower flange 902, the spindle 906, the grip 136 and/or the ratchet 530 are fabricated from a single piece of material, for example, using an injection molding process. The ratchet 530 is configured to engage the pawl 402 for holding the bobbin 134 against rotation while the floss 106 is under tension for constraining the spool against turning in a first direction and permitting the bobbin 134 to turn in a second direction. As illustrated in FIG. 5, the pawl 402 permits clockwise rotation of the bobbin 134 (in the direction of arrows 558 disposed on the spool) while preventing counter-clockwise rotation of the bobbin 134, e.g., while the floss 106 is under tension.

The bobbin lock 306 may secure the bobbin 134 within the take-up chamber 132 using snap projections 516 engaging the lower flange 902. Moreover, the snap projections 516 may be inserted into the spindle aperture 904, rendering them inaccessible once engaging the lower flange 902, thus, preventing inadvertent removal of the bobbin 134 after assembly. Two snap projections 516 are illustrated in FIG. 5, however, 1, 3, 4, 5, 6, 7, 8, 9, 10, or more snap projections 518 may be used. The take-up chamber 132 optionally includes indicia 532 configured to indicate an angular position of the bobbin grip 136. In various embodiments, 2, 3, 4, 6, 8, 12, or more indicia 532 may be disposed about the upper surface of the take-up chamber 132. An image of an arrow may be disposed on the grip 136 for indicating an angular position of the grip 136.

In various embodiments, the pawl mount 404 is secured to the handle and/or the take-up chamber 132 using adhesives, welds, fasteners, and/or the like. A pawl lock 108 illustrated in FIG. 5 (and FIGS. 1 and 3) is an example of a fastener used for securing the pawl mount 404 to the handle 102. The pawl lock 108 includes snap projections 518 for engaging an inner surface of the pawl mount 404 and securing the pawl 402. Four snap projections 518 are illustrated in FIG. 5, however, 1, 2, 3, 5, 6, 7, 8, 9, 10, or more snap projections 518 may be used. Various components are illustrated as being fabricated as a single piece, including the source spool 501; the lid 124; the bobbin 134; the pawl lock 108; the pawl mount 404 and pawl 402; the projection 112, button assembly 104, and the body 500.

FIG. 10 is a side elevation of internal parts of the flosser 100 of FIG. 1. The various components of FIG. 9 (e.g., the handle, the source chamber 122, take-up chamber 132, the head 110 the bobbin 134, the bobbin lock 306, the pawl 402 and pawl mount 404, the pawl lock 108, the button assembly 104, the lid 124, the spool 501, and the projection 112) are shown in their relative assembled positions. In some embodiments, the handle, the source chamber 122, take-up chamber 132, and the head 110 are fabricated from a single piece of material, for example using injection molding processes.

In FIG. 10, the handle, the source chamber 122, the take-up chamber 132, and the head 110 have been omitted for clarity. For illustration purposes, the remaining components in FIG. 10, including the bobbin 134, the bobbin lock 306, the pawl 402 and pawl mount 404, the pawl lock 108, the button assembly 104, the lid 124, the spool 501, and the projection 112 are shown in their assembled positions relative to the omitted parts (handle, source chamber 122, take-up chamber 132, and head 110) and to each other. The floss 106 is also shown and labeled in subsections for illustrating an exemplary path.

FIG. 9 differs from FIG. 10 in that the body 500 is omitted from FIG. 10 and the internal parts are shown in elevation instead of cross section. FIG. 9 further differs from FIG. 10 in that FIG. 9 illustrates the button assembly 104 in the engagement position, discussed elsewhere herein. FIG. 10 illustrates the button assembly 104 in the disengagement position, discussed elsewhere herein. The Button assembly 104 is configured to rotate about the pivot 522 to move the engagement pawl 524 (double arrow) between a position of engagement with the cog 502 (FIG. 9) and disengagement with the cog 502 (FIG. 10). The spring 526 may bias the button assembly 104 in a position for engaging the cog 502.

FIG. 10 further illustrates a path for routing floss 106 from the source spool 501 along the head 110 into suspension between the projection 112 and the feed guide 114, through the feed guide 114, around the source assembly 120, along the handle 102 and to the take-up bobbin 134. The path is illustrated in FIG. 10 as path segments 106a-106m.

Before use, floss 106 is wrapped around the spindle 504 of the source spool 501 at path segment 106a. Along path segment 106b, floss may pass through the first aperture 540 and along channel 542 to the second aperture 544. At path segment 106c, floss 106 may pass through the second aperture from the upper to the lower of the head 110. At path segment 106d, floss is suspended between the second aperture 544 and the projection aperture 116. At path segment 106e, floss may be suspended between the projection aperture 116 and the feed guide 114.

During use, floss 106 that is suspended between the projection aperture 116 and the feed guide 114, the projection 112 may be inserted between a brace wire or arch wire and interproximal space or contacts between a pair of adjacent teeth. Insertion of the projection 112 inserts the projection aperture 116, thus, the floss 106 below the brace wire. Thus, the floss 106 may be used for cleaning the interproximal spaces between the teeth including below the brace wire.

After use, floss 106 may traverse from the lower to the upper side of the head 110 along path segment 106f through the feed guide 114. Along path segment 106g, floss 106 may move along channel 546 from the upper end of the feed guide 114 to the third aperture 548. At path segment 106h, floss 106 may traverse from the upper side of the head 110 to the groove 408 around the source chamber 122. Groove 408 may allow gripping the source chamber 122 and manipulation of the flosser 100 without touching floss 106 as it travels around the source chamber along path segment 106i from the third aperture 548 to the fourth aperture 550. At path segment 106j, floss 106 may traverse through the fourth aperture 550 from the lower to upper side of the handle 102. Along path segment 106k, floss 106 may travel along the handle channel 552 from the source assembly 120 to the take-up assembly 130. The handle channel 552 may allow gripping the handle 102 and manipulating the flosser 100 without touching floss 106 that may have contamination and debris as the floss 106 travels the length of the handle 102 along path segment 106k from the fourth aperture 550 to the fifth aperture 554. At the path segment 106m, floss 106 passes through aperture 554 into the take-up chamber 132. After use, floss 106 may be wrapped around the spindle 906 of the take-up bobbin 134 at path segment 106a. The path including path segments 106a-106m is an example of a routing of floss 106 from a source spool to a take-up bobbin. Alternative routing of floss 106 may be used in various embodiments of the flosser 100.

Figure 11:
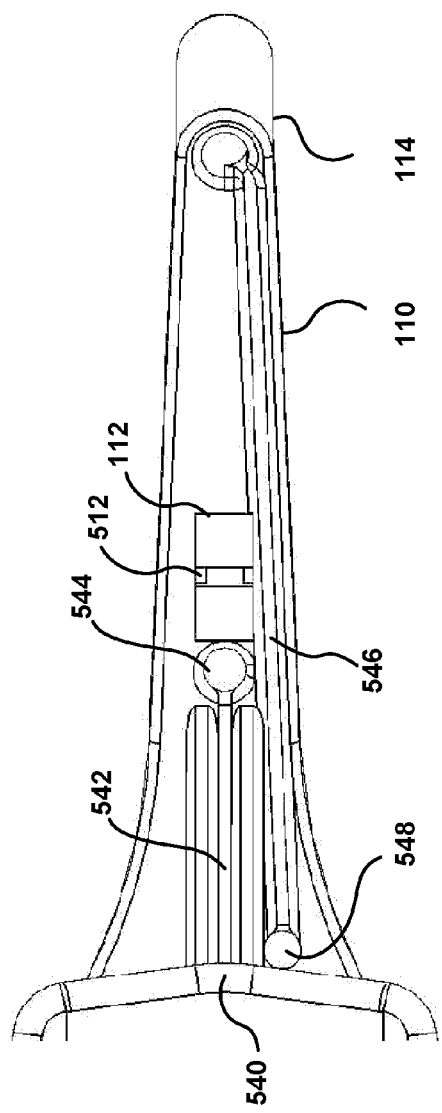
FIG. 11 is an enlargement of a portion of FIG. 3 showing details of the head of the flosser.

FIG. 11 is an enlargement of a portion of FIG. 3 showing details of the head 110 of the flosser 100. FIG. 11 illustrates details of the first aperture 540, the channel 542 the second aperture 544, the upper end of the feed guide 114, channel 546, and the third aperture 548. Additional details of the projection 112 are also illustrated.

Figure 12:
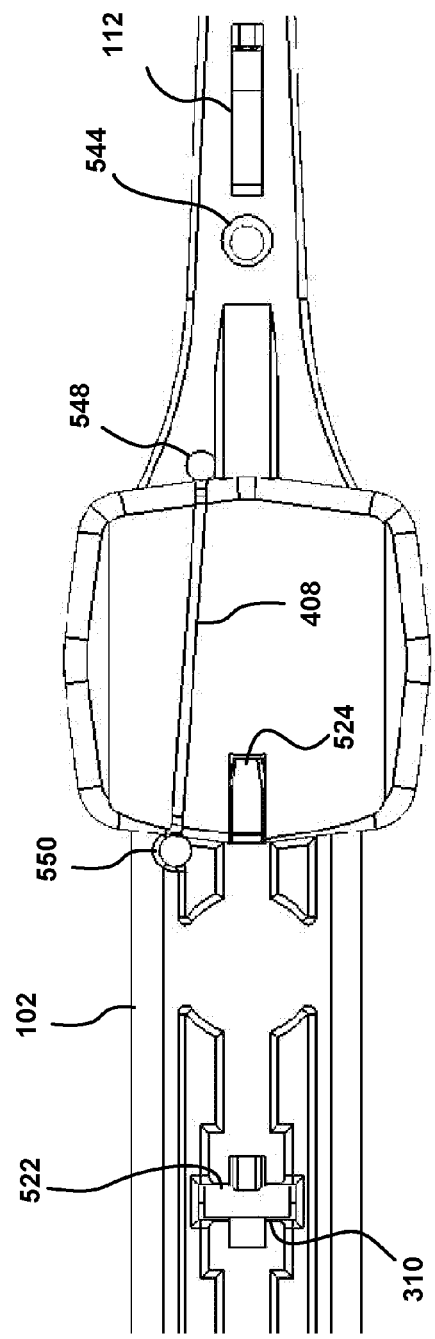
FIG. 12 is an enlargement of a portion of FIG. 4 showing details of the source chamber and portions of the head and handle.

FIG. 12 is an enlargement of a portion of FIG. 4 showing details of the source chamber 122 and portions of the head 110 and handle 102. FIG. 12 illustrates details of the second aperture 544, the third aperture 548, the fourth aperture 550, and groove 408. Additional details of the engagement pawl 524, the button socket 310 and the pivot 522 are also illustrated.

Figure 13:
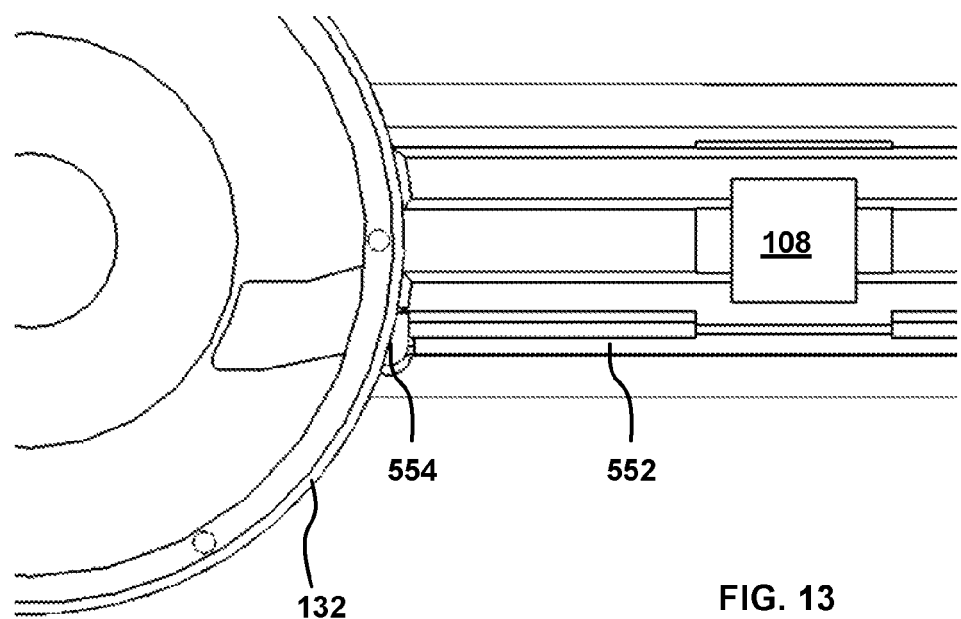
FIG. 13 is an enlargement of a portion of FIG. 3 showing details of the take-up spool and handle of the flosser of FIG. 1.

FIG. 13 is an enlargement of a portion of FIG. 3 showing details of the take-up bobbin 134 and handle 102 of the flosser 100 of FIG. 1. FIG. 13 illustrates details of a portion of the handle channel 552 and the fifth aperture 554.

Figure 14:
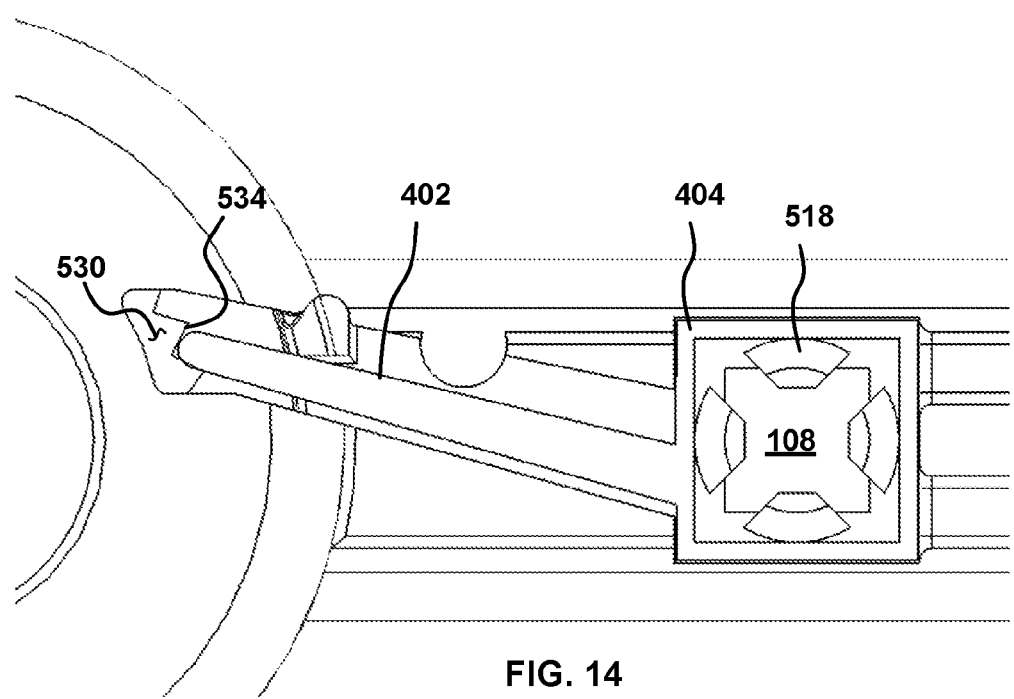
FIG. 14 is an enlargement of a portion of FIG. 4 showing details of the take-up chamber, pawl, and handle of the flosser of FIG. 1.

FIG. 14 is an enlargement of a portion of FIG. 4 showing details of the take-up chamber 132, pawl 402, and handle 102 of the flosser 100 of FIG. 1. Details of an engagement between the ratchet 530 and the pawl are illustrated. In some embodiments, the pawl is about normal to a face 534 of the ratchet. The face 534 may also be about normal to an adjacent face. For purposes of the face 534 of the ratchet, about normal is an angle less than about 12 degrees. An engagement at about a right angle minimizes backlash of the ratchet. When the face 534 of the ratchet tooth is essentially tangent to an arc described by the end of the pawl, the ratchet 530 has minimal retrograde movement as the pawl moves from the point of the ratchet tooth to the face 534. Moreover, force applied by the face 534 to the pawl is in the axis of the pawl, thus, there is minimal or no side load on the pawl. This reduces stress where the pawl 402 joins the pawl mount 404. FIG. 14 further illustrates details of engagement of the snap projections 518 in the pawl mount 404.

Figure 15:
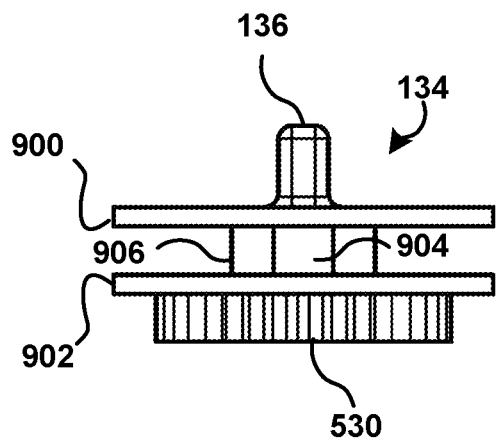
FIG. 15 is a side elevation of the take-up bobbin of FIG. 15, in accordance with aspects of the technology.
Figure 16:
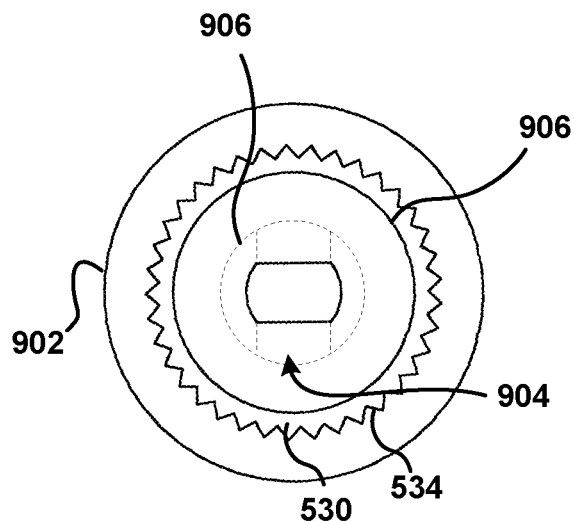
FIG. 16 is a bottom plan view of a take-up bobbin of FIG. 1, in accordance with aspects of the technology.

FIG. 15 is a side elevation of the take-up bobbin 134 of FIG. 1, in accordance with aspects of the technology. FIG. 16 is a bottom plan view of a take-up bobbin 134 of FIG. 15, in accordance with aspects of the technology. The take-up bobbin 134 of FIGS. 15 and 16 includes the spindle 906 and the spindle aperture 904. The spindle 906 and an outline of the spindle aperture 904 are shown in dotted line in FIG. 16 to indicate that they are not visible from the bottom plan view. Floss 106 may be threaded through the spindle aperture 904 and secured to the spindle 906, e.g., using a knot. Upon rotating the take-up bobbin 134, floss may wrap around the spindle 906. The take-up bobbin 134 may further include an upper flange 900 and a lower flange 902. The upper flange 900 is configured to contain debris and contamination within the take-up chamber 132. The lower flange 902 is configured to support the ratchet 530 and prevent floss 106 from tangling about the ratchet 530 and the pawl 402.

In some embodiments, antimicrobial agents are infused into the floss 106 for inhibiting transfer of bacteria between surfaces of teeth, braces, and from one contact to another. For example, floss 106 may be permeated with chlorhexidine gluconate to inhibit survival of bacterial and other microbes in the floss 106 during use and to inhibit deposition of microbes on the surfaces of teeth, contacts, and/or braces. Various antimicrobial agents include chlorhexidine gluconate, Triclosan, hydrogen peroxide, carbamide peroxide, and cetylpyridinium chloride. Environmentally friendly antimicrobial agents may be used, including an extract of magnolia bark, xylitol (a sugar alcohol that is naturally occurring in Birch and fruits), and antimicrobial peptides, which are compounds that are found throughout the animal and plant kingdom such as HNP (human neutrophil proteins). The floss 106 may also be infused with anti-cavity agents such as florides, e.g., sodium fluoride, hexafluorosilicic acid ($H_2SiF_6$) and its salt sodium hexafluorosilicate ($Na_2SiF_6$), and/or the like. The floss 106 may also be used for depositing the antimicrobial and/or anti-cavity agents on the surfaces of teeth and/or braces. In some embodiments, the antimicrobial agent may be applied to the floss 106 as the floss 106 is dispensed from the source spool 501 during use. For example, the floss 106 may be routed through a reservoir of antimicrobial agent (not illustrated) disposed on the handle 102, the head 110, on the source chamber 122, and/or within the source chamber 122. The reservoir may be configured to apply the antimicrobial agent to the floss 106 during transit. The above antimicrobial and anti-cavity agents may be used individually or in various combinations and mixtures.

Figure 17:
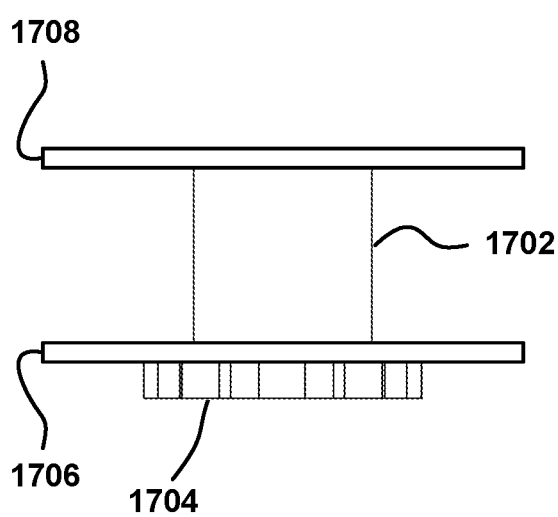
FIG. 17 is a side elevation of an alternative embodiment of the source spool of FIG. 5, in accordance with aspects of the technology.

FIG. 17 is a side elevation of an alternative embodiment of the source spool of FIG. 5, in accordance with aspects of the technology. The source spool 1700 differs from the source spool 501 of FIG. 5 in that the source spool 1700 includes a lower flange 1706 and an upper flange 1708. The source spool 1700 includes a spindle 1702 and a cog 1704, similar to the spindle 504 and the cog 502, respectively, of the source spool 501. The lower flange 1706 and upper flange 1708 are configured to prevent tangling of floss 106 during winding onto the source spool 1700. Some types of automated winding equipment fail to sense a transition between the spindle the cog 1704 resulting in an attempt to wind floss 106 too close to, or even onto, the cog 1704 with undesirable results. The lower flange 1706 reduces winding of floss 106 on the spindle 1702 too close or onto the cog 1704. The upper flange 1708 serves to prevent floss 106 from slipping off of the spindle 1702 during winding.

In some embodiments, the floss 106 is impregnated with an anti-microbial agent. Examples of anti-microbial agents include 5-chloro-2-(2,4-dichlorophenoxy)phenol (Triclosan), chlorhexidine gluconate, hydrogen peroxide, carbamide peroxide, and cetylpyridinium chloride. Environmentally friendly antimicrobial agents may be used, including an extract of magnolia bark, xylitol (a sugar alcohol that is naturally occurring in Birch and fruits), and antimicrobial peptides, which are compounds that are found throughout the animal and plant kingdom such as HNP (human neutrophil proteins). The floss 106 may also be infused with anti-cavity agents such as florides, e.g., sodium fluoride, hexafluorosilicic acid ($H_2SiF_6$) and its salt sodium hexafluorosilicate ($Na_2SiF_6$), and/or the like. The floss 106 may also be used for depositing the antimicrobial and/or anti-cavity agents on the surfaces of teeth and/or braces. In some embodiments, the antimicrobial agent may be applied to the floss 106 as the floss 106 is dispensed from the source spool 501 during use. For example, the floss 106 may be routed before use through a reservoir (not illustrated) of antimicrobial agent disposed on the handle 102, in the source chamber 122, or external to the source chamber 122. The reservoir may be configured to apply the antimicrobial agent to the floss 106 during transit. The above antimicrobial and anti-cavity agents may be used individually or in various combinations and mixtures.

An unexpected problem in using the flosser 100 described above is that in some instances the floss breaks. This can happen due to a variety of causes. For example, fillings may have sharp edges resulting in abrasion or cutting the floss. In another example, a strand floss may wear out after repeated uses. Typically after flossing contacts between four different pairs of teeth, the floss segment 106e suspended between the projection 112 and the feed guide 114 may become frayed and weakened. Continuing to floss becomes more and more likely to cause the floss to break at path segment 106e. In some instances, the floss has a weak section, for example, due to a splice used by the factory to join two different rolls of floss. In some instances, the floss can catch on braces. A solution is to retie the floss to the bobbin 134. This can be done by wrapping multiple turns of an end of the broken floss 106 around the spindle 906 of the bobbin 134 at segment 106m. However, another problem then arises in that the bobbin 134 may be difficult to remove from the take-up chamber 132 for retying or rewrapping, and then may be difficult to reinstall into the take-up chamber 132. Providing for simple removal and retaliation of the bobbin creates a risk of small parts that can be dropped and/or lost.

Another solution to retying broken floss is to provide structures in the take-up chamber and/or take-up bobbin for retying floss to the bobbin without out removing the bobbin from the take-up chamber. In an alternative embodiment, a retie flange may be fabricated along or adjacent a horizontal channel in the upper flange of the bobbin. The aperture 554 adjacent the channel 552 may be extended into a vertical retie slot that may also be fabricated in the take-up chamber. The retie flange may be a flap cut out of the upper flange. The flap may be bent at a slight upward angle from the upper flange to extend above the upper surface of the upper flange. The retie flange may form an opening or channel in the upper flange and the angle of the flap may also serve as a ramp adjacent the opening.

Floss can be run along the opening to the grip of the bobbin, and then wrapped around the grip. Inverted bevels or undercuts on the ends of the grip may prevent the wrappings of floss from slipping off the grip. The button 520 may release the source spool for allowing the floss to play out freely as the bobbin is rotated by a user.

As the bobbin is rotated, the floss may enter the opening of the retie flange to be captured under the ramp portion of the retie flange. The ramp portion of the retie flange may then force the floss down into the retie slot in the take-up chamber. Inside the take-up chamber, the floss may wrap around the spindle of the bobbin as the bobbin is further rotated by the user. After several complete rotations of the bobbin, the wrapped floss may grip the spindle. Once the floss grips the spindle, the button may be released and tension applied to the floss by further rotation of the bobbin.

Optionally, the end of the floss wrapped around the grip may be snipped off and discarded. FIGS. 18-25 illustrate an alternative embodiment of a flosser for retying broken floss, and retying the floss without removing a take-up bobbin from a take-up chamber of the flosser.

Figure 18:
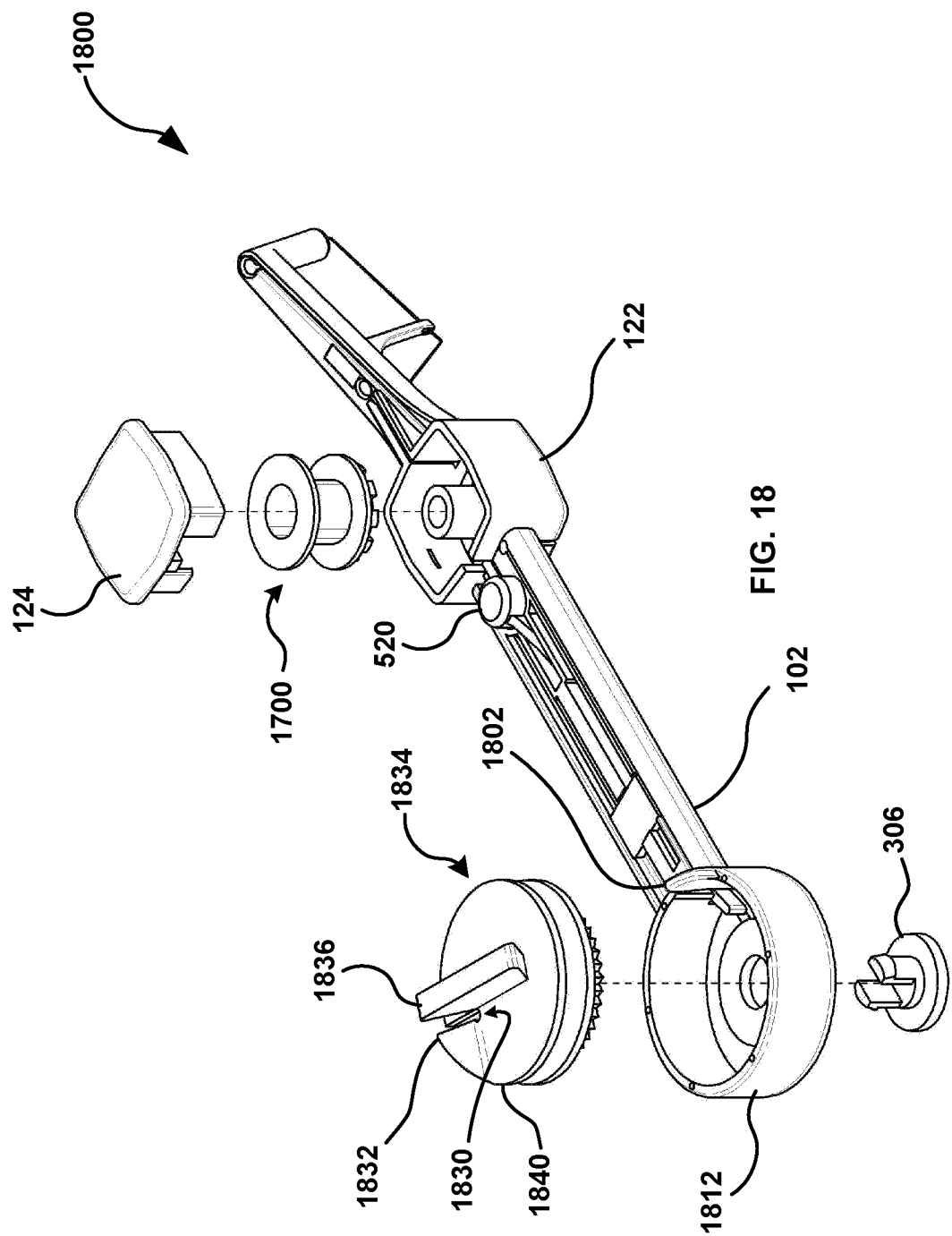
FIG. 18 is an exploded perspective view of an alternative embodiment of a flosser, illustrating exemplary internal components, in accordance with aspects of the technology.

FIG. 18 is an exploded perspective view of an alternative embodiment of a flosser 1800, illustrating exemplary internal components for retying floss 106, in accordance with aspects of the technology. The flosser 1800 of FIG. 18 differs from the flosser 100 illustrated in FIGS. 1-17 in that flosser 1800 includes a take-up bobbin 1834 and a take-up chamber 1812 are configured for retying broken floss without removing the bobbin 1834 from the take-up chamber 1812.

The bobbin 1834 differs from the bobbin 134 in that the bobbin 1834 includes a grip 1836 and an upper flange 1840 configured for retying floss 106. The upper flange 1840 of bobbin 1834 differs from the upper flange 900 of bobbin 134 in that the a retie flange 1832 and a channel 1830 are disposed in the upper flange 1840. The retie flange 1832 extends upward from the upper flange 1840 and may be bent to extend at an angle above the upper flange 1840. In various embodiments the angle between the upper flange 1840 and the retie flange is about 2, 4, 5, 6, 8, 10, 15, 20, or 30 degrees. The retie flange 1832 may also extend above the rim of the take-up chamber 1812. The retie flange 1832 is configured for capturing floss while the bobbin 1834 is being rotated. The retie flange 1832 is further configured for urging the floss 106 down into a winding position around the spindle 906, as the bobbin 1834 is being rotated. The channel 1830 is configured to admit the floss into a space between the upper flange 1840 and the lower flange 902 for winding around the spindle 906.

Figure 19A:
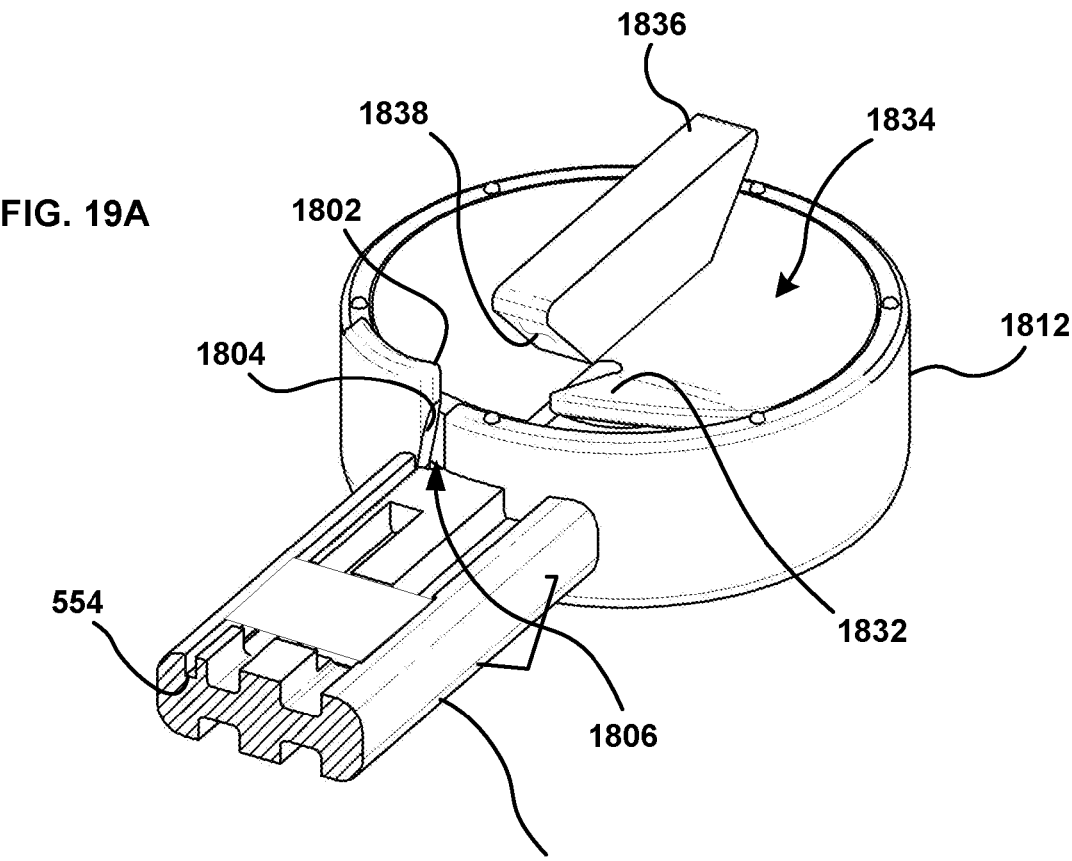
FIG. 19A is a left front perspective view of an exploded diagram of a bobbin and take-up chamber of FIG. 18.
Figure 19B:
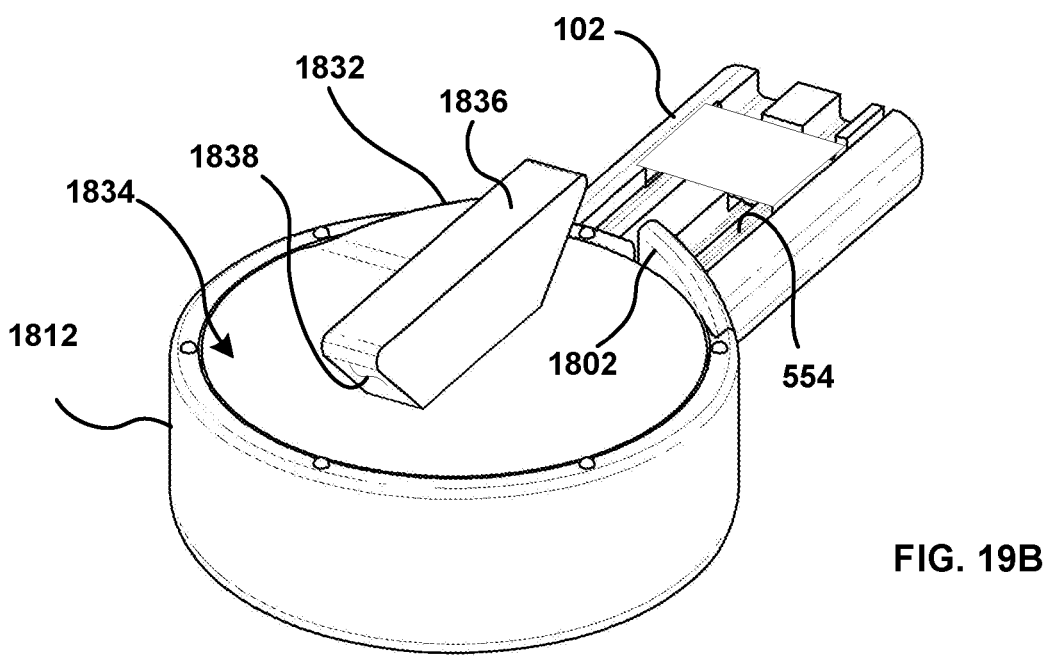
FIG. 19B is a right rear perspective view of the take-up chamber and the bobbin of FIG. 18.

FIG. 19A is a left front perspective view of an exploded diagram of the bobbin 1834 and the take-up chamber 1812 of FIG. 18. FIG. 19B is a right rear perspective view of the bobbin 1834 positioned within the take-up chamber 1812 of FIG. 18. Portions of the flosser 1800 have been omitted for clarity. The take-up chamber 1812 of FIG. 19A differs from the take-up chamber 132 of FIGS. 1-17 in that the take-up chamber 1812 includes a retie slot 1806. The retie slot 1806 includes a capture fence 1802 extending above a rim of the take-up chamber 1812 The capture fence 1802 is configured for capturing floss 106 while rotating the bobbin 1834. The retie slot 1806 further includes a guide edge 1804 configured for urging the floss down into the retie slot 1806.

The grip 1836 of the bobbin 1834 differs from the grip 136 of the bobbin 134, in that the grip 1836 includes reverse or inverted bevels, or undercuts that form ears or horns 1838 at either end of the grip 1836. The grip 1836 may resemble a cleat used for boats and the undercuts may form triangular structures similar to horns on cleats. The horns 1838 serve to facilitate winding of the floss 106 around the grip 1836 during retying (illustrated elsewhere herein) to secure the floss 106 to the grip 1836. The horns 1838 may hold windings of the floss 106 on the grip 1836 in a manner similar to cleats. The horns 1838 may prevent the floss 106 from slipping off the grip 1836 while turning the bobbin 1834, e.g., using the grip 1836. The horns 1838 may further serve to hold a length of the floss 106 adjacent a plane of the upper flange 1840.

Figure 20A:
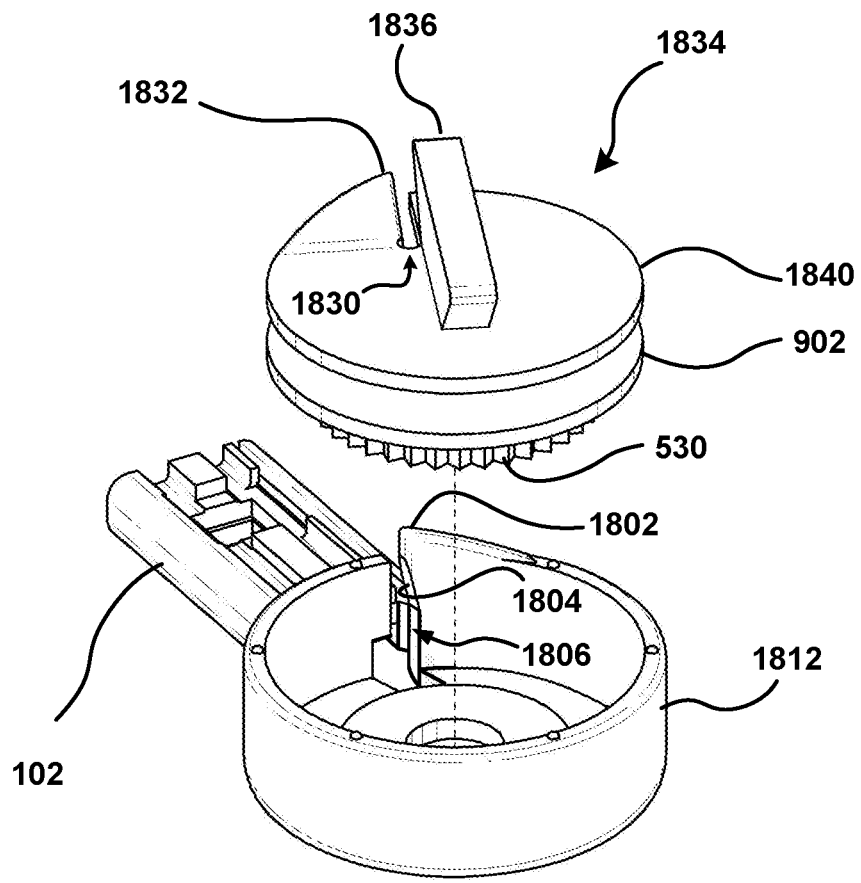
FIG. 20A is a left rear perspective view of an exploded diagram of the bobbin and the take-up chamber of FIG. 18.
Figure 20B:
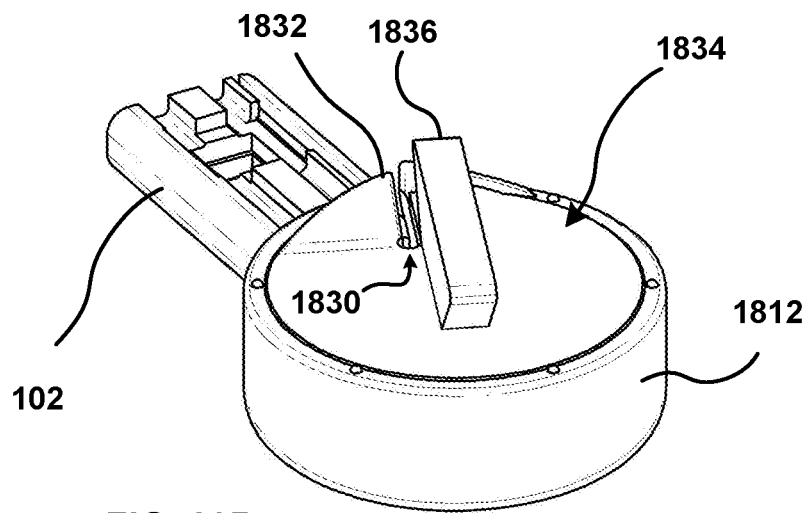
FIG. 20B is a left rear perspective view showing the bobbin disposed within the take-up chamber of FIG. 18.

FIG. 20A is a left rear perspective view of an exploded diagram of the bobbin 1834 and take-up chamber 1812 of FIG. 18. FIG. 20B is a left rear perspective view of the take-up chamber 1812 showing the bobbin 1834 disposed within the take-up chamber. Portions of the flosser 1800 have been omitted for clarity. FIG. 20B differs from FIG.

19B in that the retie channel 1830 in FIG. 20B, is in alignment with the retie slot 1806.

Figure 21A:
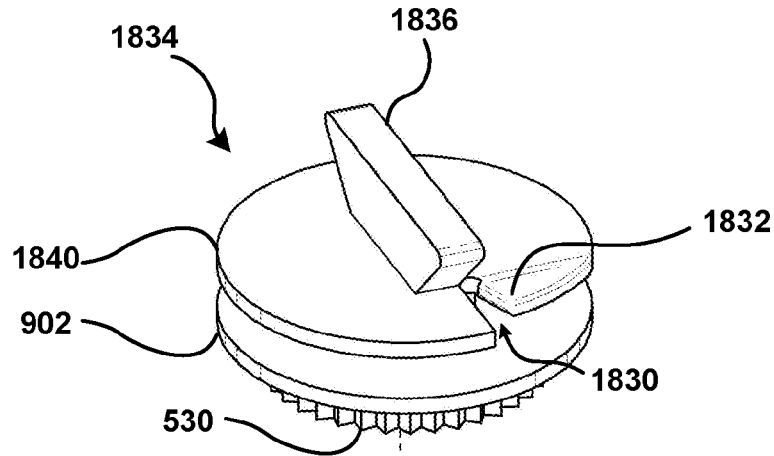
FIG. 21A is a right front perspective view of an exploded diagram of the bobbin and the take-up chamber of FIG. 18.
Figure 21B:
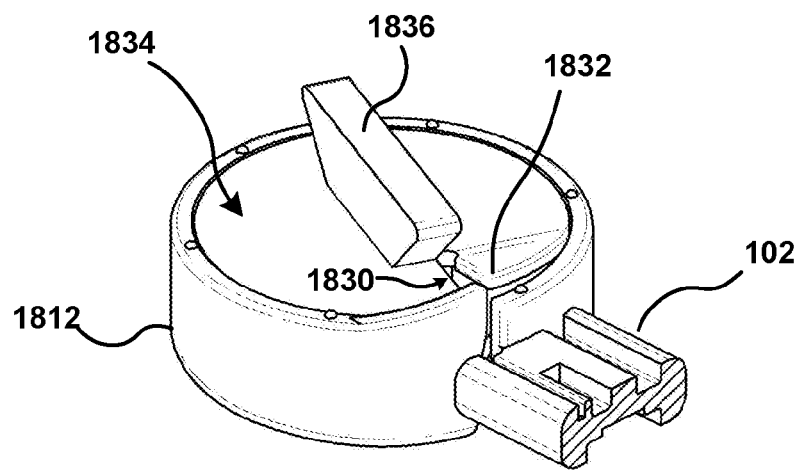
FIG. 21B is a right front perspective view showing the bobbin disposed within the take-up chamber of FIG. 18.

FIG. 21A is a right front perspective view of an exploded diagram of the bobbin 1834 and the take-up chamber 1812 of FIG. 18. FIG. 21B is a right front perspective view showing the bobbin 1834 disposed within the take-up chamber 1812 of FIG. 18. Portions of the flosser 1800 have been omitted for clarity. The channel 1830 in FIG. 21B also is aligned with the retie slot 1806.

FIGS. 22A-22D illustrate views of the bobbin 1834 from various angles. FIG. 22A is a top plan view of the bobbin 1834 of FIG. 18. FIG. 22B is a side elevation view of the bobbin 1834 of FIG. 18. The horns 1838 in the grip 1836 are illustrated in FIG. 22B as having an undercut of about 45 degrees. However, in various embodiments, the undercut of the horns 1838 may be a range of about 5 to 80 degrees. FIG. 22C is a front elevation view of the bobbin 1834 of FIG. 18. FIG. 22D is a bottom perspective view of the bobbin 1834 of FIG. 18. In some embodiments, the grip 1836, horns 1838, upper flange 1840, lower flange 902, spindle 906, ratchet 530, retie flange 1832, and retie channel 1830 are fabricated as one single entire unitary piece.

FIGS. 23A-23D are front perspective views illustrating application of a rotation to the bobbin 1834 for retying floss 106 on the flosser 1800 of FIG. 18. FIGS. 24A-24D are top plan views of the corresponding positions of the bobbin 1834 of FIGS. 23A-23D, respectively, for illustrating the application of the rotation to the bobbin 1834 for retying floss 106 on the flosser 1800 of FIG. 18. Portions of the flosser 1800 have been omitted for clarity.

FIG. 23A is a right front perspective view illustrating an initial orientation of the bobbin 1834 with respect to the take-up chamber 1812 for wrapping floss 106 around the grip 1836. Descriptions of FIG. 23A may be considered with reference to FIG. 25B, which is an enlargement of portions of FIG. 23A. FIG. 24A is a top plan view illustrating an initial orientation of the bobbin 1834 with respect to the take-up chamber 1812 for wrapping floss 106 around the grip 1836. In FIGS. 23A and 24A, the floss 106 is illustrated as being wrapped around the grip 1836 about one and a half times for simplicity. However, the floss 106 may be wrapped two or three turns (or more around the grip 1836. Tension may be applied to the floss 106 during wrapping. The horns 1838 may capture and hold the floss on the grip 1836. The floss 106 may be arranged to traverse the retie slot 1806 about adjacent the capture fence 1802 for wrapping. The free end of the floss is illustrated as being loose. However, the free end of the floss 106 may be held against the grip 1836 (e.g., by hand) during rotation of the bobbin 1834. The floss 106 is illustrated using a dotted line for clarity. The horns 1838 may extend to the surface of the upper flange 1840. Tension applied to the floss 106 during wrapping may serve to urge the floss 106 downward to an intersection of the grip 1836 and the surface of the upper flange 1840 as the floss 106 is wrapped around the grip 1836. Thus, the horns 1838 may position floss 106 proximate the upper surface of the upper flange 1840 and in suspension between the guide edge 1804 and the retie flange 1832. As illustrated in FIG. 23A, the retie flange 1832 may be seen to extend above the upper surface of the upper flange 1840 and, thus, above the floss 106.

From the initial orientation of the bobbin 1834 illustrated in FIGS. 23A and 24A, the bobbin 1834 may be rotated a few degrees to capture the floss 106 between the retie flange 1832 and the guide edge 1804. The button 520 may be pressed and held during rotation of the bobbin 1834. As the bobbin 1834 is rotated, the capture fence 1802 may maintain the floss 106 proximate the retie slot 1806 and in alignment with the channel 1830 until the retie flange 1832 captures the floss 106. The retie flange 1832 may then act as a ramp to apply a force on the floss downward into the retie slot 1806, as well as sideways against the capture fence 1802. As the bobbin 1834 continues to rotate the retie flange 1832 may progressively force the floss 106 downward along guide edge 1804.

The guide edge 1804 may include an angle configured to bias movement of the floss 106 in a downward direction into the retie slot 1806. The angle of the guide edge 1804 may also serve to prevent the floss from exiting back up and out of the retie slot 1806 over the capture fence 1802. That is, the angle of the guide edge 1804 may apply additional force on the floss 106 in a downward direction into the retie slot 1806. In various embodiments of the flosser 1800, the guide edge 1804 is about 2, 5, 10, 15, 20, 25, 30, or more degrees. Thus, the retie flange 1832 may urge the floss 106 against the guide edge 1804, such that both the retie flange 1832 and the guide edge 1804 form a scissors-like action to push the floss downward into the retie slot 1806. In some embodiments, the guide edge 1804 also includes a curve. The curve of the guide edge 1804 may be convex or concave.

Figure 24C:
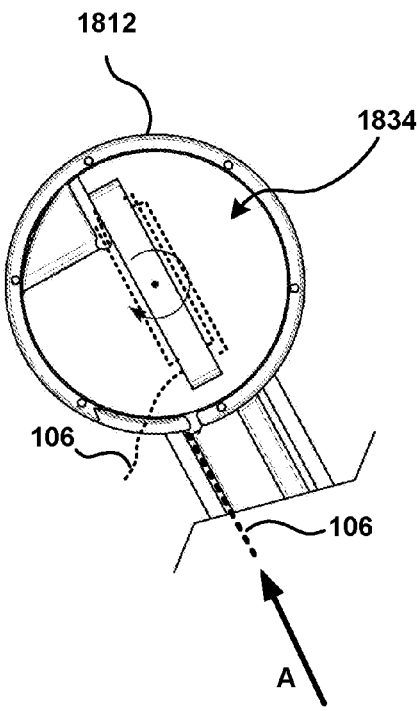
Figure 25A:
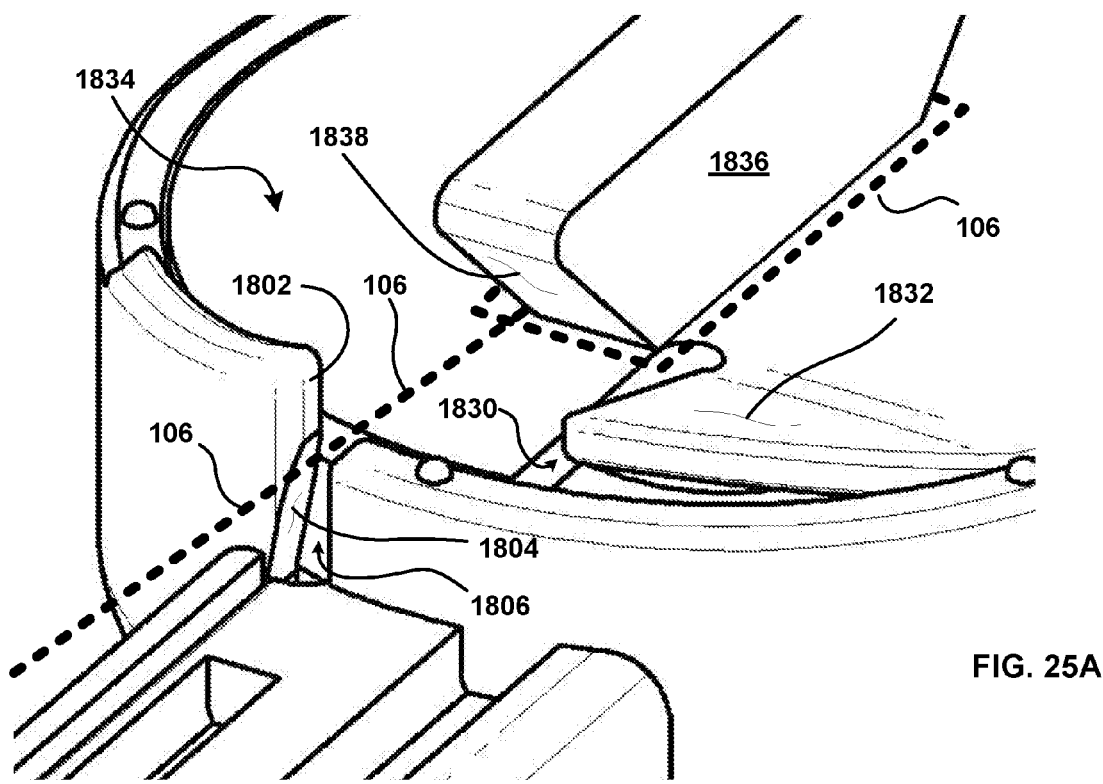
FIG. 25A is an enlargement of a portion of FIG. 19A.
Figure 25B:
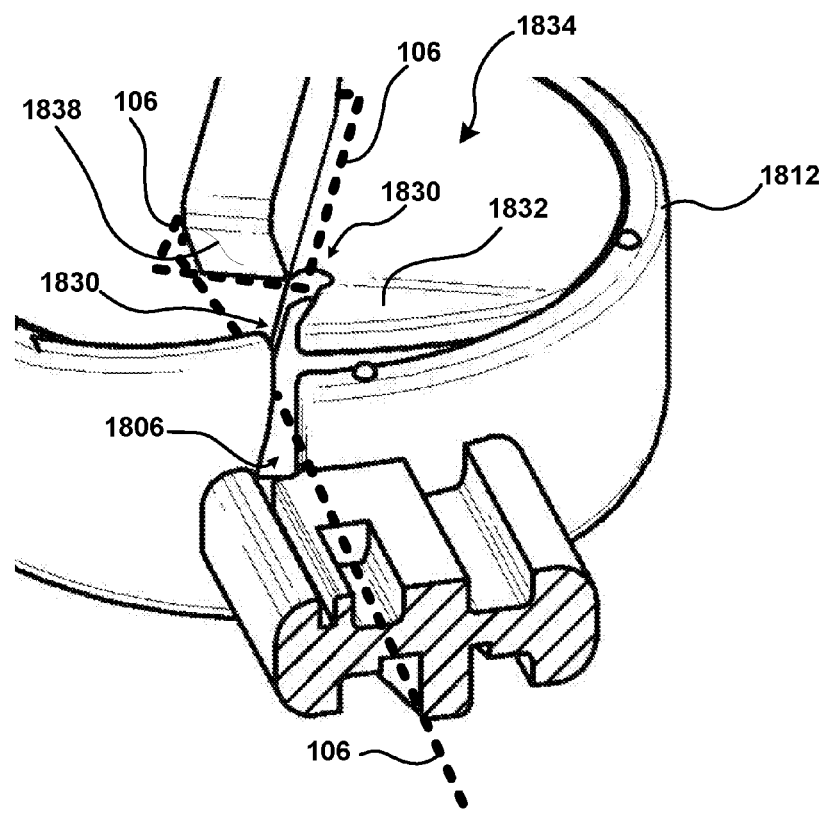
FIG. 25B is an enlargement of a portion of FIG. 23A.

In the initial orientation of the bobbin 1834 for wrapping floss 106 around the grip 1836 (as illustrated in FIGS. 23A, 24A, and 25B) the channel 1830 is approximately aligned with the retie slot 1806. However, the initial orientation of the bobbin 1834 within the take-up chamber 1812 may be at any angle with respect to the retie slot 1806. Other orientations may result in a larger angle through which the bobbin 1834 will be rotated in order to capture the floss 106 between the retie flange 1832 and the capture fence 1802 or guide edge 1804. For example, FIG. 25A is an enlargement of FIG. 19A illustrating an alternative initial orientation of the bobbin 1834 for wrapping floss 106 around the grip 1836. The bobbin 1834 may be rotated clockwise an additional number of degrees to reach the initial position illustrated in FIGS. 23A and 24A. In some orientations of the bobbin 1834, the capture fence 1802 may be used to constrain the floss in a position proximate the retie slot 1806 while wrapping the floss 106 around the grip 1836. Examples of such orientations include angles between the channel 1830 and the retie slot 1806 that are greater than 10 degrees and less than 170 degrees.

FIG. 23B and FIG. 24B are a right front perspective view and a top plan view, respectively, illustrating an orientation of the bobbin 1834 after rotation of the bobbin 1834 about ninety degrees clockwise (about a quarter of a turn) from alignment of the channel 1830 with the retie slot 1806. In the orientation illustrated in FIGS. 23B and 24B, the floss 106 is beginning to wrap around the spindle 906 (not visible in these views). The arrow A indicates the direction of advance of the floss 106 as wrapping of the floss 106 around the spindle 906 draws the floss 106 into the take-up chamber 1812. In the orientation of FIGS. 23B and 24B, the upper flange 1840 closes off the upper end of the retie slot 1806 such that the floss 106 is constrained within the retie slot 1806. Effectively, the retie slot 1806 has become an aperture through which the floss has been threaded by the rotation of the bobbin 1834 and action of the retie flange 1832. Once the floss 106 is thus threaded, the floss 106 may engage the spindle 906 of the bobbin 1834. The button 520 may continue to be pressed and held during rotation of the bobbin 1834.

Figure 23C:
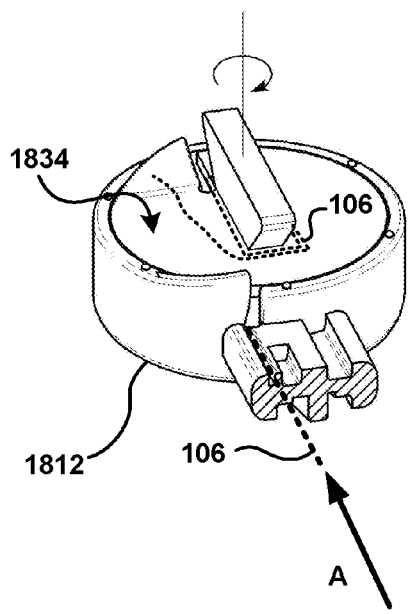

FIG. 23C and FIG. 24C are a right front perspective view and a top plan view, respectively, illustrating an orientation of the bobbin 1834 after rotation of the bobbin 1834 about one hundred eighty degrees clockwise (about half a turn) from initial alignment of the channel 1830 with the retie slot 1806. In the orientation illustrated in FIGS. 23C and 24C, the floss 106 continues wrapping around the spindle 906. The arrow A indicates the direction of continued advance of the floss 106 as wrapping of the floss 106 around the spindle 906 draws the floss 106 into the take-up chamber 1812. The upper flange 1840 continues to close off the upper end of the retie slot 1806 turning the retie slot 1806 into an aperture through which the floss is threaded to engage the spindle 906 of the bobbin 1834.

Figure 23D:
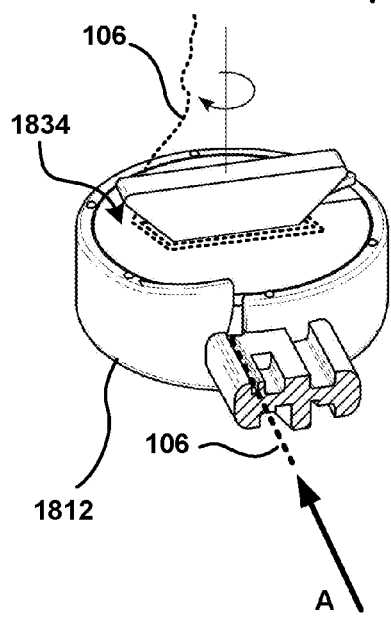
Figure 24D:
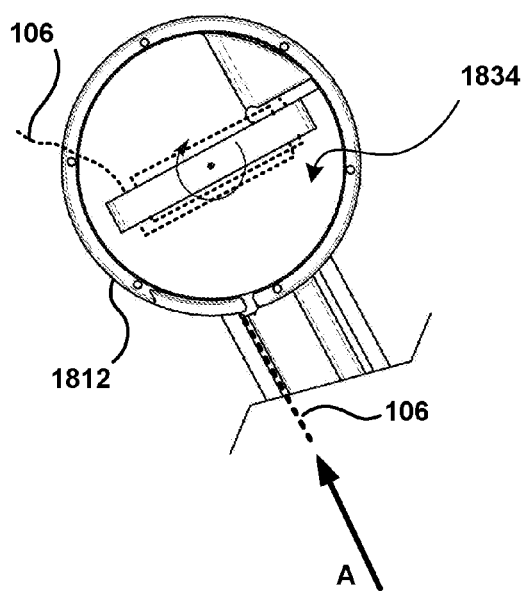

FIG. 23D and FIG. 24D are a right front perspective view and a top plan view, respectively, illustrating an orientation of the bobbin 1834 after rotation of the bobbin 1834 about two hundred seventy degrees clockwise (about three-quarters of a turn) from initial alignment of the channel 1830 with the retie slot 1806. In the orientation illustrated in FIGS. 23D and 24D, the floss 106 continues wrapping around the spindle 906. The upper flange 1840 continues to close off the upper end of the retie slot 1806 turning the retie slot 1806 into an aperture through which the floss is threaded to engage the spindle 906 of the bobbin 1834. The arrow A indicates the direction of continued advance of the floss 106 as wrapping of the floss 106 around the spindle 906 draws the floss 106 into the take-up chamber 1812.

Once wrapping of the floss 106 around the spindle 906 has been initiated and the floss is feeding freely through the retie slot 1806, the bobbin 1834 may continue to be rotated through several complete turns. Additional complete turns may be applied to provide subsequent layers of floss 106 that are wound on top of the initial layers. The button 520 may continue to be pressed and held during rotation of the bobbin 1834 through these multiple complete turns.

The subsequent top layers of floss 106 may bind the initial lower layers of floss 106 to the spindle 906. The arrow A indicates the direction of continued advance of the floss 106 as wrapping of the floss 106 through multiple turns around the spindle 906 draws the floss 106 into the take-up chamber 1812. Typically 2, 3, 4, 5, 6, 7, 8, or 10 complete turns may be applied to provide subsequent layers of floss 106 wound on top of the initial layers that are sufficient to secure the floss 106 to the spindle 906. Once the number of turns of the bobbin 1834 is sufficient to secured the floss 106, the spindle 906, the button 520 may be released. Tension may then be applied to the floss 106 by rotating the bobbin 1834 to test how strongly the floss 106 grips the spindle 906. If slip is detected, the button 520 may be pressed and held while additional turns of the bobbin 1834 wrap additional layers of floss 106 onto the spindle 906. The button 520 may again be released to test for slip. If slip is still detected, the process may be repeated until the floss is firmly secured to the bobbin 1834 and no slip is detected. Optionally, the excess floss 106 wrapped around the grip 1836 is off and discarded.

FIG. 25A is an enlargement of FIG. 19A illustrating an alternative initial orientation of the bobbin 1834 for wrapping floss 106 around the grip 1836. Portions of the flosser 1800 have been omitted for clarity. In the enlargement of FIG. 25A, a gap may be seen where the retie flange extends above a rim of the take-up chamber 1812.

FIG. 25B is an enlargement of FIG. 23A illustrating the channel 1830 in a position for wrapping floss 106 around the grip 1836. Portions of the flosser 1800 have been omitted for clarity. The enlargement illustrates the retie flange 1832 about to ride over the floss 106 and force the floss 106 down into the retie slot 1806.

The embodiments discussed herein are illustrative. As these embodiments are described with reference to illustrations, various modifications or adaptations of the methods and/or specific structures described may become apparent to persons of ordinary skill in the art. Various features and aspects of the above described technology may be used individually or jointly. Features in each of the various illustrations may be combined with features in other illustrations or used individually for illustrating the present technology. All such modifications, adaptations, or variations that rely upon the teachings of the embodiments, and through which these teachings have advanced the art, are considered to be within the spirit and scope of the present application. Hence, these descriptions and drawings should not be considered in a limiting sense, as it is understood that the present application is in no way limited to only the embodiments illustrated.

What is claimed is:

1. A flosser comprising:
   a handle;
   a head including a first and second floss support for suspending floss therebetween, the second floss support including an aperture sized for feeding the floss into suspension between the first and second floss supports, the second floss support shaped for insertion of the aperture into a space between the wire brace and two adjacent teeth for cleaning an interproximal space between the two teeth using suspended floss;
   a source chamber coupled to a first end of the handle and configured to support the head, the source chamber enclosing a source spool for dispensing floss to the aperture in the second floss support;
   a button configured to release tension on the floss;
   a take-up chamber coupled to a second end of the handle opposite the source chamber, the take-up chamber and the source chamber external to the handle, the take-up chamber having a retie slot proximate the handle, the retie slot including a capture fence extending above a rim of the take-up chamber and a guide edge configured to bias floss into the retie slot;
   a take-up bobbin disposed in the take-up chamber for receiving used floss, the take-up bobbin including a retie flange extending at an angle above the rim of the take-up chamber, the retie flange and the guide edge configured to trap the floss and to urge the floss into the retie slot while rotating the take-up bobbin;
   a grip disposed on the take-up bobbin, the grip configured for wrapping a broken end of the floss around the grip, wherein the grip includes a horn on either end of the grip, the horns configured for holding the floss on the grip while wrapping a broken end of the floss around the grip.

2. The flosser of claim 1, wherein the capture fence is configured to constrain the floss proximate the retie slot during rotation of the take-up bobbin.

3. The flosser of claim 1, wherein the capture fence is configured to constrain the floss proximate the retie slot during wrapping of the broken end of the floss a the grip.

4. The flosser of claim 1, wherein the horns are further configured to dispose the floss adjacent and about parallel to an upper flange of the take-up bobbin.

5. The flosser of claim 1, wherein the take-up bobbin further includes an upper flange, a lower flange, a spindle, and a ratchet, the retie flange extending at an angle from the upper flange.

6. The flosser of claim 5, wherein the grip, the retie flange, the upper flange, the lower flange, the spindle, and the ratchet are fabricated as one single entire unitary piece.

7. A method for retying broken floss on a flosser including a pair of projections for suspending the floss, the method comprising:

rotating a take-up bobbin including a retie channel disposed in an upper flange to align the retie channel with a retie slot disposed in a take-up chamber, the retie channel adjacent a retie flange extending upward from and above the upper flange;

wrapping an end of the broken floss around a grip of a take-up bobbin, wherein the grip includes a horn on either end of the grip, the horns configured for holding the floss on the grip while wrapping the end of the broken floss around the grip;

pressing a button to release source spool to rotate freely;

rotating the take-up bobbin to position a portion of the retie flange above the floss after wrapping the end of the broken floss around the grip;

further rotating the take-up bobbin to urge the floss against a guide edge of the retie slot;

further rotating the take-up bobbin to close a top of the retie slot using the upper flange;

further rotating the take-up bobbin at least two complete turns to wrap the floss around a spindle of the take-up bobbin until the floss is secured to the spindle;

releasing the button; and rotating the take-up bobbin to apply tension to the floss suspended between the pair of projections.

8. The method of claim 7, further comprising pressing the button and pulling a length of floss from the source spool before wrapping the end of the broken floss around the grip.

9. The method of claim 8, further comprising re-threading the floss through a handle of the flosser, a head of the flosser, and at least one of the projections.

10. The method of claim 7, further comprising holding an end of the floss against the grip while rotating the take-up bobbin.

11. The method of claim 7, further comprising:

a) detecting slip of the floss on the spindle when applying tension;

b) pressing the button;

c) further rotating the take-up bobbin at least two additional complete turns to wrap additional floss around a spindle of the take-up bobbin;

d) releasing the button;

e) rotating the take-up bobbin to apply tension to the floss and detect slipping;

f) repeating steps b-e if slip of the floss on the spindle is detected when applying tension.

12. The method of claim 7, further comprising removing floss wrapped around the grip of the take-up bobbin.

13. The method of claim 7, wherein the guide edge forms an angle with respect to the retie slot, the angle of the guide edge configured to force the floss into the retie slot.

14. The method of claim 7, wherein the ends of the grip form an angle configured to hold the floss wound around the grip and against the upper flange.

15. A retiable flosser comprising:

a head including a pair of projections configured to support floss suspended therebetween;

a source chamber supporting the head;

a handle coupled to the source chamber;

a take-up chamber coupled to the handle;

a bobbin rotatably disposed in the take-up chamber, the bobbin including an upper flange, a lower flange, a spindle for winding floss between the upper and lower flanges, and a grip for rotating the bobbin, wherein the grip includes an undercut forming a horn configured for holding floss on the grip while wrapping floss around the grip;

a retie slot disposed in the take-up chamber proximate the handle;

a capture fence extending above a rim of the take-up chamber, the capture fence configured to constrain floss above the retie slot while wrapping floss around the grip;

a guide edge disposed along one side of the retie slot, the guide edge forming an angle configured for forcing floss into the take-up chamber while rotating the bobbin;

a retie channel disposed in the upper flange; and a retie flange forming one edge of the retie channel, the retie flange extending above a plane of the upper flange and above a rim of the take-up chamber, the retie flange configured for forcing floss against the guide edge and into the retie slot while rotating the bobbin using the grip, the grip further configured for receiving at least two wraps of floss around the grip and holding wraps of floss adjacent the upper flange while rotating the bobbin.

16. The flosser of claim 15, further comprising a longitudinal channel along the handle for providing free movement of used floss along the handle while gripping the handle, the longitudinal channel aligned with the retie slot.

17. The flosser of claim 15, wherein the grip, the retie flange, the upper flange, the lower flange, the spindle, and a ratchet are fabricated as one single entire unitary piece.

18. The flosser of claim 15, wherein the horn is further configured to dispose a portion of the floss adjacent a plane of the upper flange.

* * * * *